(12) United States Patent
Chen et al.

(10) Patent No.: US 11,117,888 B2
(45) Date of Patent: Sep. 14, 2021

(54) IRREVERSIBLE INHIBITORS OF PYRUVATE KINASE M2 AND THE USE THEREOF

(71) Applicant: China Medical University, Taichung (TW)

(72) Inventors: Ching-Shih Chen, Taichung (TW); Hsiang-Wen Lin, Taichung (TW); Chih-Shiang Chang, Taichung (TW); Po-Chen Chu, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 29 days.

(21) Appl. No.: 16/748,843

(22) Filed: Jan. 22, 2020

(65) Prior Publication Data

US 2021/0221801 A1    Jul. 22, 2021

(51) Int. Cl.
| | |
|---|---|
| *C07D 413/06* | (2006.01) |
| *C07D 231/12* | (2006.01) |
| *C07D 207/337* | (2006.01) |
| *A61P 35/00* | (2006.01) |

(52) U.S. Cl.
CPC ............ *C07D 413/06* (2013.01); *A61P 35/00* (2018.01); *C07D 207/337* (2013.01); *C07D 231/12* (2013.01)

(58) Field of Classification Search
CPC . C07D 413/06; C07D 207/337; C07D 231/12
See application file for complete search history.

(56) References Cited

FOREIGN PATENT DOCUMENTS

WO    WO-2018026811 A2 *    2/2018 ........... A61K 31/404

OTHER PUBLICATIONS

Wong, N.; Ojo, D.; Yan, J.; Tang, D., PKM2 Contributes to Cancer Metabolism. Cancer Lett 2015, 356, 184-191.
Iqbal, M. A.; Gupta, V.; Gopinath, P.; Mazurek, S.; Bamezai, R. N., Pyruvate Kinase M2 and Cancer: An Updated Assessment. FEBS Lett 2014, 588, 2685-2692.
Christofk, H. R.; Vander Heiden, M. G.; Harris, M. H.; Ramanathan, A.; Gerszten, R. E.; Wei, R.; Fleming, M. D.; Schreiber, S. L.; Cantley, L. C., The M2 Splice Isoform of Pyruvate Kinase Is Important for Cancer Metabolism and Tumour Growth. Nature 2008, 452, 230-233.
Luo, W.; Semenza, G. L. Emerging Roles of PKM2 in Cell Metabolism and Cancer Progression. Trends Endocrinol Metab 2012, 23, 560-566.
Yang, Y. C.; Cheng, T. Y.; Huang, S. M.; Su, C. Y.; Yang, P. W.; Lee, J. M.; Chen, C. K.; Hsiao, M.; Hua, K. T.; Kuo, M. L., Cytosolic PKM2 Stabilizes Mutant Egfr Protein Expression through Regulating Hsp90-Egfr Association. Oncogene 2016, 35, 3387-3398.
Chen, L.; Tang, Z.; Wang, X.; Ma, H.; Shan, D.; Cui, S., PKM2 Aggravates Palmitate-Induced Insulin Resistance in Hepg2 Cells via Stat3 Pathway. Biochem Biophys Res Commun 2017,492,109-115.
Yang, W.; Xia, Y.; Ji, H.; Zheng, Y.; Liang, J.; Huang, W.; Gao, X.; Aldape, K.; Lu, Z., Nuclear PKM2 Regulates Beta-Catenin Transactivation Upon Egfr Activation. Nature 2011,480,118-122.
Vander Heiden, Matthew G; Christofk, Heather R; Schuman, Eli; Subtelny, Alexander 0; Sharfi, Hadar; Harlow, Edward E; Xian, Jun; Cantley, Lewis C., Identification of small molecule inhibitors of pyruvate kinase M2. Biochem. Pharmacol. 2010, 79, 1118-1124.
Chen, J.; Xie, J.; Jiang, Z.; Wang, B.; Wang, Y.; Hu, X., Shikonin and Its Analogs Inhibit Cancer Cell Glycolysis by Targeting Tumor Pyruvate Kinase-M2. Oncogene 2011, 30,4297-4306.
Li, Wenjuan; Liu, Joan; Zhao, Yunfeng, PKM2 inhibitor shikonin suppresses TPA-induced mitochondrial malfunction and proliferation of skin epidermal JB6 cells. Mol. Carcinog. 2014, 53,403-412.
Ning, X.; Qi, H.; Li, R.; Li, Y.; Jin, Y.; McNutt, M. A.; Liu, J.; Yin, Y., Discovery of Novel Naphthoquinone Derivatives as Inhibitors of the Tumor Cell Specific M2 Isoform of Pyruvate Kinase. Eur. J. Med. Chem. 2017, 138, 343-352.

* cited by examiner

*Primary Examiner* — Kamal A Saeed
(74) *Attorney, Agent, or Firm* — Hannah Tien

(57) ABSTRACT

The invention provides a novel class of propiolylamide-based irreversible inhibitors of PKM2 compounds of the general formula I, pharmaceutical compositions, and methods of inducing an anti-tumor effect in a subject suffering from tumor comprising administering to the subject a pharmaceutical composition comprising an effective amount of compound of formula I.

17 Claims, 10 Drawing Sheets

Specification includes a Sequence Listing.

(A)
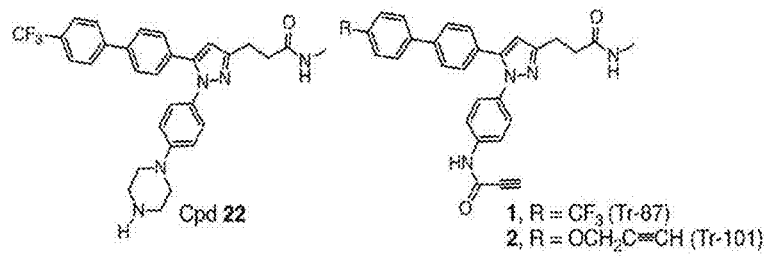
(B)
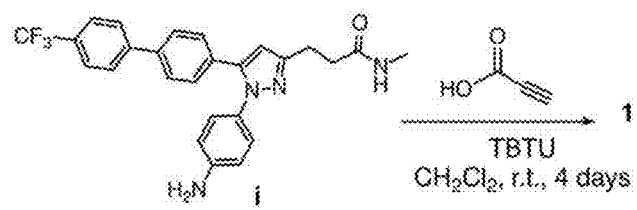
(C)
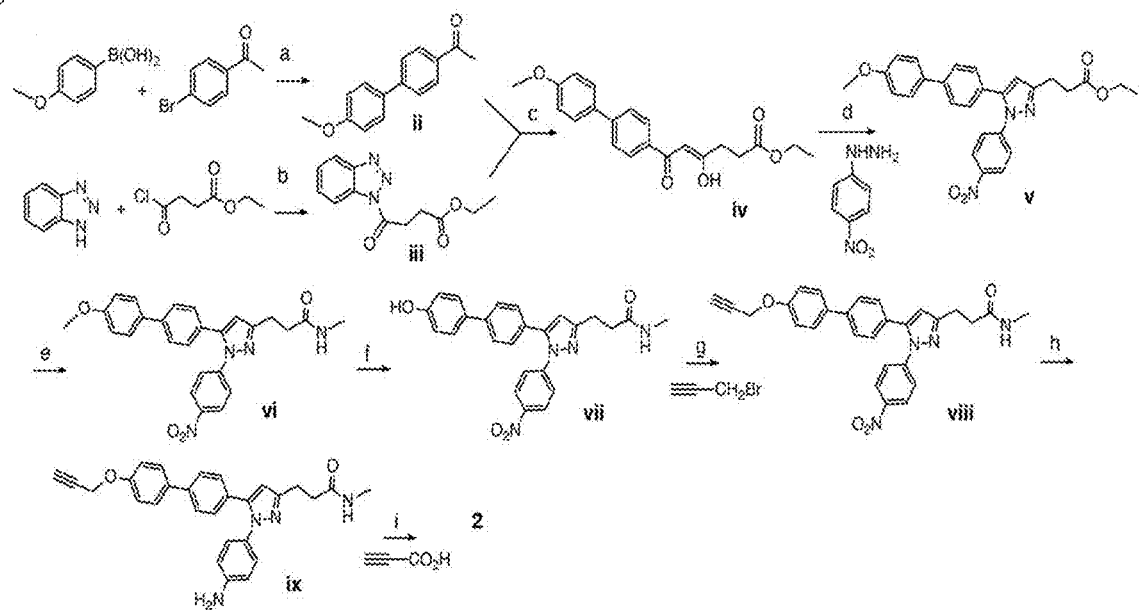
Figure 2

(A)
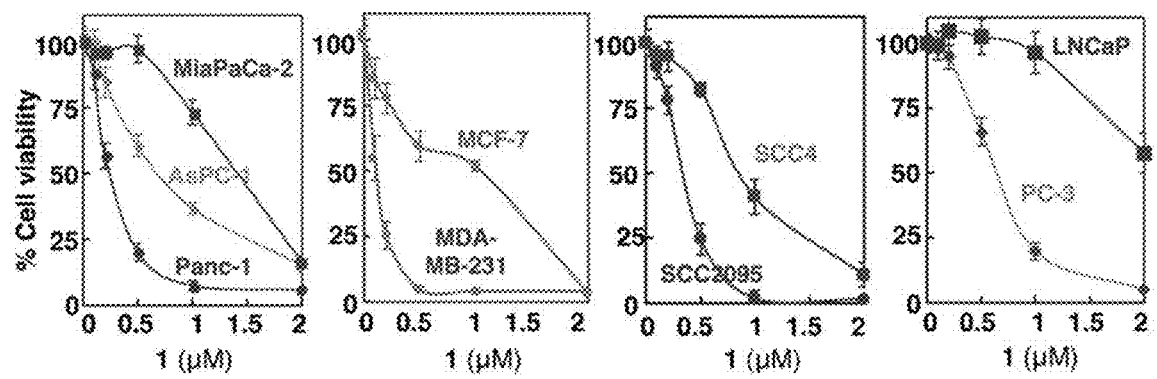
(B)
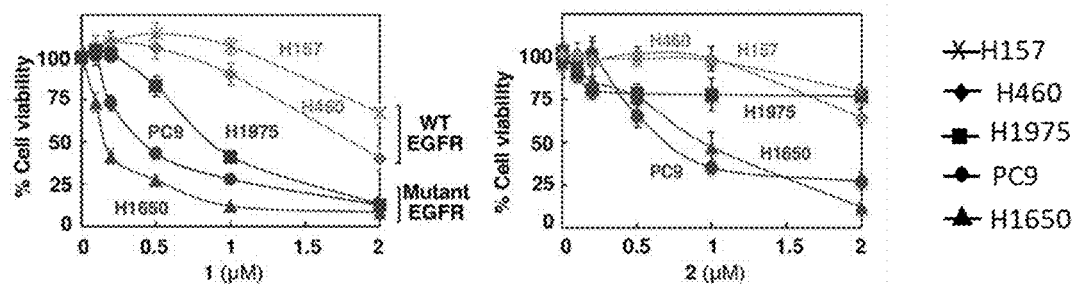
Figure 3

(A)

| Target proteins | | MOSCOT score | Peptide sequence |
|---|---|---|---|
| KPYM_HUMAN | Pyruvate kinase PKM | 1653 | VFLAQK |
| LDHA_HUMAN | L-lactate dehydrogenase | 1618 | NVKIFK |
| CISY_HUMAN | Citrate synthase | 152 | GLVYETSVLDPDEGIR |
| MDHM_HUMAN | Malate dehydrogenase | 130 | IFGVTTLDIVR |
| ACLY_HUMAN | ATP-citrate synthase | 114 | VKSTNPDMR |
| ENOA_HUMAN | Alpha-enolase | 113 | VVIGMDVAASEFFR |
| PCKGM_HUMAN | Phosphoenolpyruvate carboxylase | 81 | STFIGLVPK |
| ACSF3_HUMAN | Acyl-CoA synthetase family member 3 | 43 | NVLAPYAVPSKLVLVEEIPR |
| PGK1_HUMAN | Phosphoglycerate kinase 1 | 36 | VLPGVDLSKI |

(B)

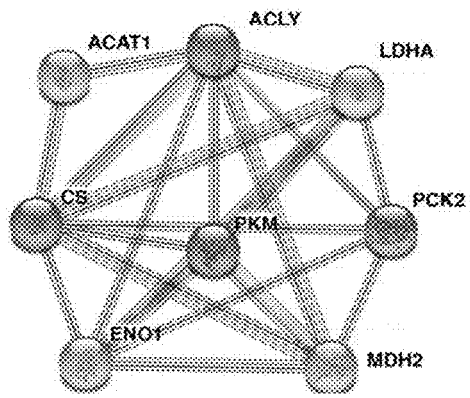

(C)

| | Biological Process (GO) | | |
|---|---|---|---|
| Pathway ID | Pathway description | False Disc. rate | Matching proteins in network |
| GO.0006091 | Generation of precursor Metabolism and energy | 0.00161 | ACLY, CS, ENO1, LDHA, PKM |
| GO.0006096 | Glycolytic process | 0.00186 | ENO1, LDHA, PKM |
| GO.0019674 | NAD metabolic process | 0.00186 | ENO1, LDHA, PKM |
| GO.0005975 | Carbohydrate metabolic process | 0.00334 | ACLY, ENO1, LDHA, PCK2, PKM |
| GO.0055114 | Oxidation-reduction process | 0.00823 | ACLY, CS, ENO1, LDHA, PKM |
| GO.0006006 | Glucose metabolic process | 0.0145 | ENO1, PCK2, PKM |
| GO.0044723 | Single-organism carbohydrate process | 0.0265 | ENO1, LDHA, PCK2, PKM |
| GO.0061621 | Canonical glycolysis | 0.028 | ENO1, PKM |
| GO.0006101 | Citrate metabolic process | 0.035 | ACLY, CS |
| GO.0046128 | Purine nucleotide metabolic process | 0.0476 | ACLY, ENO1, LDHA |

Figure 5

(A)
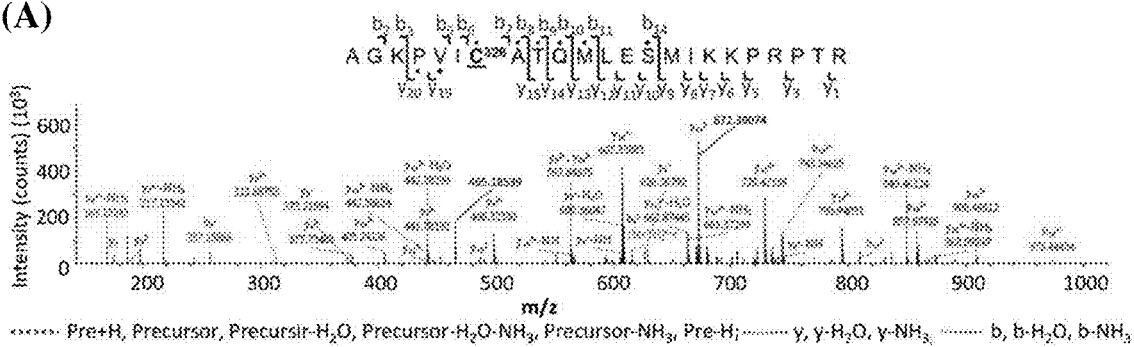
(B)
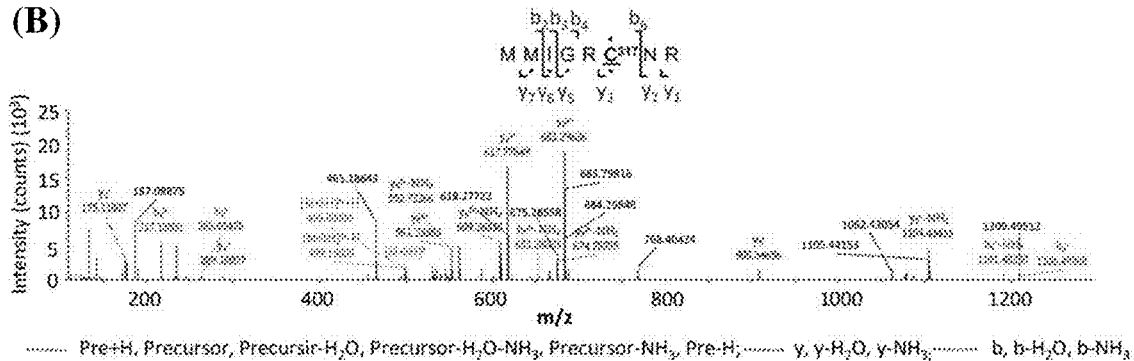
(C)
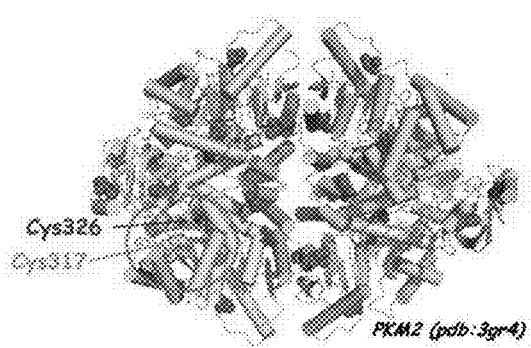
Figure 7

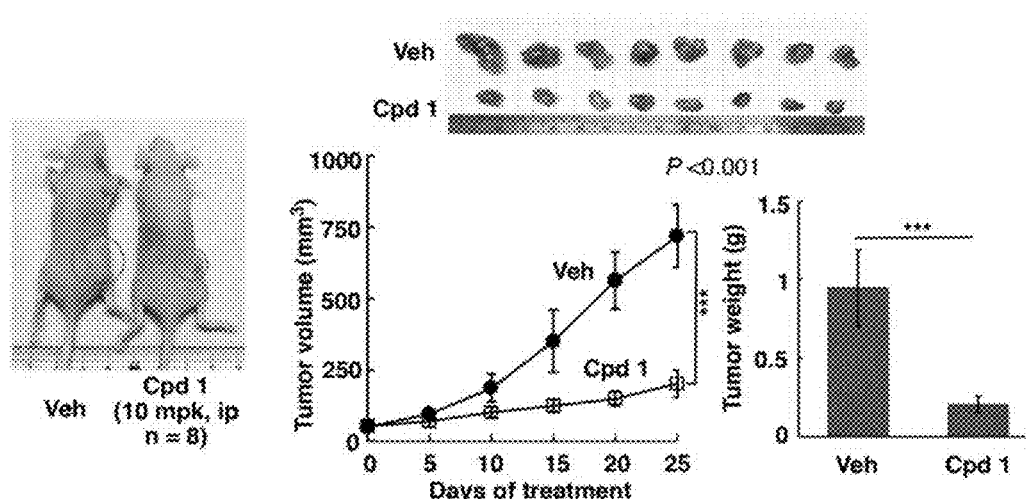
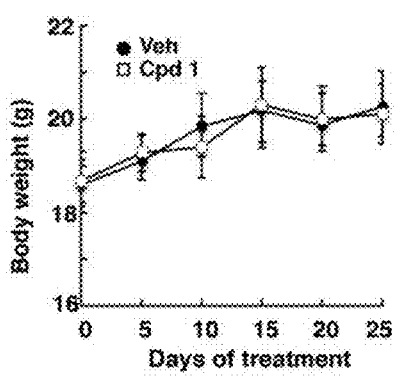
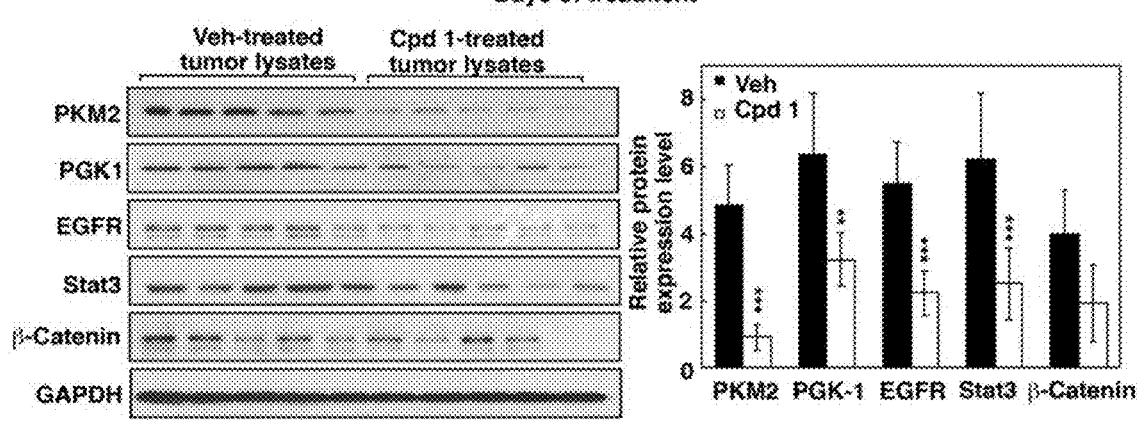
Figure 9

IRREVERSIBLE INHIBITORS OF PYRUVATE KINASE M2 AND THE USE THEREOF

This application contains a Sequence Listing in an ASCII text file, the file name is 3377-CMU-SequenceListing, the creation date is Mar. 9, 2020 and the size of the ASCII text file is 668 bytes. The material in the ASCII text file is incorporated in its entirety by reference.

FIELD OF THE INVENTION

The present invention relates to a novel class of propiolylamide-based irreversible inhibitors of PKM2 and the use of treating cancer.

BACKGROUND OF THE INVENTION

It is well recognized that cancer cells undergo metabolic shift to a glycolytic phenotype in the course of tumorigenesis (the so-called Warburg effect), which provides tumor cells with survival advantages under unfavorable growth environments. Evidence indicates that this metabolic reprogramming necessitates cancer cells to upregulate the expression of key regulators of the glycolytic pathway, including glucose transporter 1, hexokinase 2, and the M2 splice form of pyruvate kinase (PKM2) (Cancer Lett 2015, 356, 184-191; FEBS Lett 2014, 588, 2685-2692; Nature 2008, 452, 230-233). From a therapeutic perspective, these glycolytic regulators represent promising targets for cancer drug development, among which PKM2 has received much attention in light of its multifaceted function in promoting tumor growth and progression. PKM2 catalyzes the rate-limiting step of glycolysis, i.e., conversion of phosphoenolpyruvate (PEP) to pyruvate. In addition, PKM2 also regulates the transcription of various cancer-associated genes upon entering the nucleus where it activates a number of transcription factors through physical interactions and/or phosphorylation (Cancer Lett 2015, 356, 184-191; FEBS Lett 2014, 588, 2685-2692; Endocrinol Metab 2012, 23, 560-566).

Beyond its function as a metabolic regulator, PKM2 has also been reported to activate a number of oncogenic effectors through physical interactions in different cellular compartments, leading to increased protein stability [i.e., EGFR (Biochem. Pharmacol. 2010, 79, 1118-1124)] or phosphorylation [i.e., Stat3 (Oncogene 2011, 30, 4297-4306), and β-catenin (Eur. J. Med. Chem. 2017, 138, 343-352)] of these oncogenic effectors.

To date, multiple structurally diverse small-molecule PKM2 modulators have been developed in the past decade (Curr Pharm Des 2014, 20, 2595-2606; Oncogene 2016, 35, 3387-3398). These PKM2 inhibitors (e.g., shikonin and alkannin) (Med. Chem. Lett. 2010, 20, 3387-3393) or activators (e.g., NCGC00030335) (J. Med. Chem. 2018, 61, 4155-4164; J. Med. Chem. 2011, 54, 6364-6374) and micheliolide (Oncogene 2016, 35, 3387-3398) could suppress cancer cell proliferation by interfering with energy metabolism and/or PKM2's nuclear translocation, which underscores the crucial function of PKM2 in maintaining the malignant phenotype of cancer cells.

It is well documented that in the course of tumor progression, cancer cells adopt glycolytic phenotype to gain growth advantage and invasiveness in face of adverse environments. Mechanistically, aggressive cancer cells are more relying upon glycolysis for survival relative to nonaggressive cancer cells. As a consequence, cancer cells with a glycolytic/aggressive phenotype will be more susceptible to the antiproliferative activity of PKM2 inhibitors relative to those with non-glycolytic phenotype. Thus, from a therapeutic perspective, PKM2 inhibitors have clinical applications for the treatment of aggressive, drug-resistant cancers, including, but not limited to triple-negative breast cancer, castration-resistant prostate cancer, oral cancer, colon cancer, EGFR mutant lung cancer, and pancreatic cancer.

The past decade has witnessed an increasing interest in the development of irreversible inhibitors of the kinase cysteinome as the majority of kinases contains cysteine residues located near the catalytic domain. In principle, covalent kinase inhibitors offer several advantages over conventional ATP competitors, which include improved biochemical efficacy, high degree of selectivity, and favorable pharmacokinetic behaviors (Biochem Biophys Res Commun 2017, 492, 109-115; Nature 2011, 480, 118-122). The utility of this strategy is manifested by the FDA approval of four acrylamide-based covalent kinase inhibitors since 2013, including those targeting BTK (ibrutinib), EGFR (afatinib and osimertinib), and HER2 (neratinib), as well as many other irreversible inhibitors currently under preclinical development.

The importance of PKM2 as a cancer therapeutic target and the discovery of a series of natural product- or naphthoquinone-based reversible PKM2 inhibitors, none of which, however, has reached the stage of preclinical development. Our invention involved the development of the first-in-class irreversible PKM2 inhibitors, which contain a propiolylamide electrophile as a "war head" at the terminus. We obtained evidence that this propiolylamide moiety could selectively target the Cys326 and Cys317 residues of PKM2, leading to the inactivation and/or protein destabilization of PKM2 in cancer cells. These novel irreversible PKM2 inhibitors are structurally distinct from the aforementioned inhibitors reported in the literature, and display a discriminative antiproliferative effect toward aggressive cancer cells, relative to non-aggressive cancer cells, though the inhibition of PKM2 signaling.

DETAILED DESCRIPTION OF THE INVENTION

The present invention provides a novel class of propiolylamide-based irreversible inhibitors of PKM2 by coupling the embodied amine core structures with a propiolyl moiety (FIG. 1), which could act as an electrophilic warhead to irreversibly modify the cysteine residues of target proteins. These compounds can provide significant antitumor activity against a variety of tumor cells, especially those with aggressive phenotype. The present invention involved the development of the first-in-class irreversible PKM2 inhibitors, which contain a propiolylamide electrophile as a "war head" at the terminus. The propiolylamide moiety could selectively target the Cys326 and Cys317 residues of PKM2, leading to the inactivation and/or protein destabilization of PKM2 in cancer cells. These novel irreversible PKM2 inhibitors are structurally distinct from the PKM2 inhibitors reported in previously literatures, and display a discriminative antiproliferative effect toward aggressive cancer cells, relative to non-aggressive cancer cells, though the inhibition of PKM2 signaling.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is an aryl group that is attached to the remainder of the structure by an intervening alkyl group, whereas an aralkyl group is an aryl group that is attached directly to the structure but that includes one or more additional alkyl groups attached thereto. In the context of the present invention, suitable organic groups for the compounds of the invention are those that do not interfere with the desired activity of the compounds (e.g., their anticancer activity). In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., C1-C4 alkyl groups are alky groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclobutyl, cyclobutylmethyl, cyclopentyl, and cyclohexyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. The aryl groups may include a single aromatic ring, a plurality of separate aromatic rings, or a fused aromatic ring system. Carbocyclic aromatic rings do not include heteroatoms. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula —C(O)—NR$_1$R$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with one or more nonperoxidic O, N, S, or F substituents or other conventional substituents such as methyl groups. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein in any of their pharmaceutically acceptable forms, including isomers, tautomers, salts, solvates, polymorphs, prodrugs, and the like. It should be understood that the term "compound" includes any or all of such forms, whether explicitly stated or not (although at times, "salts" are explicitly stated).

Bioisosteres is a molecule resulting from the exchange of an atom or of a group of atoms with an alternative, broadly similar, atom or group of atoms. The objective of a bioisosteric replacement is to create a new molecule with similar biological properties to the parent compound. In medicinal chemistry, bioisosteres are chemical substituents or groups with similar physical or chemical properties which produce broadly similar biological properties to another chemical compound. Therefore, the atoms between carbon and nitrogen or oxygen and sulfur are bioisosteric replacement.

"Treat", "treating", and "treatment", etc., as used herein, refer to any action providing a benefit to a subject afflicted with a condition or disease such as cancer, including improvement in the condition through lessening or suppression of at least one symptom, delay in progression of the disease, etc.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

One aspect of the invention provides a number of compounds that have been prepared, including the compounds of formula I:

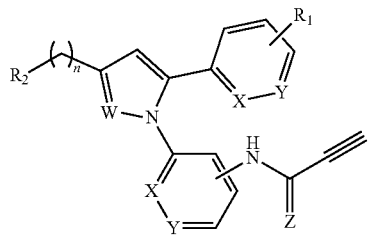

Formula 1 wherein

R₁ is independently selected from aryl, heteroaryl or heterocyclyl in any position, optionally substituted with halogen, $C_1$-$C_6$ alkyl, $C_2$-$C_6$ alkenyl, $C_2$-$C_6$ alkynyl, CN, haloalkyl, alkylamino, or $C_{1-6}$ alkoxy;

R₂ is independently selected from —C(=O) NR₃R₄ or —C(=S) NR₃R₄ wherein R₃ and R₄ are the same or different and each is H, $C_1$-$C_6$ alkyl, branched alkyl, $C_2$-$C_6$ alkenyl, branched alkenyl, or $C_3$-$C_6$ cycloalkyl which is optionally substituted with OH, CN, methoxy, $C_1$-$C_6$ alkyloxyalkyl, $C_1$-$C_6$ alkylamino, $C_1$-$C_6$ alkylaminoalkyl, aryl, heteroaryl, cycloalkyl, or heterocycloalkyl;

W is independently selected from carbon or nitrogen;

X and Y are independently selected from carbon or nitrogen;

Z is independently selected from oxygen or sulfur; and n is independently selected from 1 to 6.

In one aspect of the invention, preferably, wherein W is nitrogen.

In another aspect of the invention, preferably W is carbon.

In another aspect of the invention, more preferably W is nitrogen or carbon, preferably z is oxygen.

In another aspect of the invention, preferably R₁ is phenyl in any position, optionally substituted with halogen, $C_1$-$C_6$ alkyl, $C_2$-$C_6$ alkenyl, $C_2$-$C_6$ alkynyl, CN, haloalkyl, alkylamino, or $C_{1-6}$ alkoxy; preferably W is nitrogen, Z is oxygen.

In another aspect of the invention, more preferably R₁ is trifluoromethyl-phenyl or (prop-2-yn-1-yloxy) benzene.

In another aspect of the invention, preferably R₂ is —C(=O) NR₃R₄ wherein R₃ and R₄ are the same or different and each is H, $C_1$-$C_6$ alkyl, branched alkyl, $C_2$-$C_6$ alkenyl, branched alkenyl, or $C_3$-$C_6$ cycloalkyl which is optionally substituted with OH, CN, methoxy, $C_1$-$C_6$ alkyloxyalkyl, $C_1$-$C_6$ alkylamino, $C_1$-$C_6$ alkylaminoalkyl, aryl, heteroaryl, cycloalkyl, or heterocycloalkyl;

Preferably R₂ is (methylamino)-carbonyl or 5-methyl-1,3,4-oxadiazol-2-yl.

More preferred the compound of the present invention is N-(4-(5-(4-(ethynyloxy)-[1,1'-biphenyl]-4-yl)-3-(3-(methylamino)-3-oxo-propyl)-1H-pyrazol-1-yl) phenyl)propiolamide named as compound 2.

In another aspect of the invention, preferred compounds of the invention are compounds 1 and 3-5 which have the following structures:

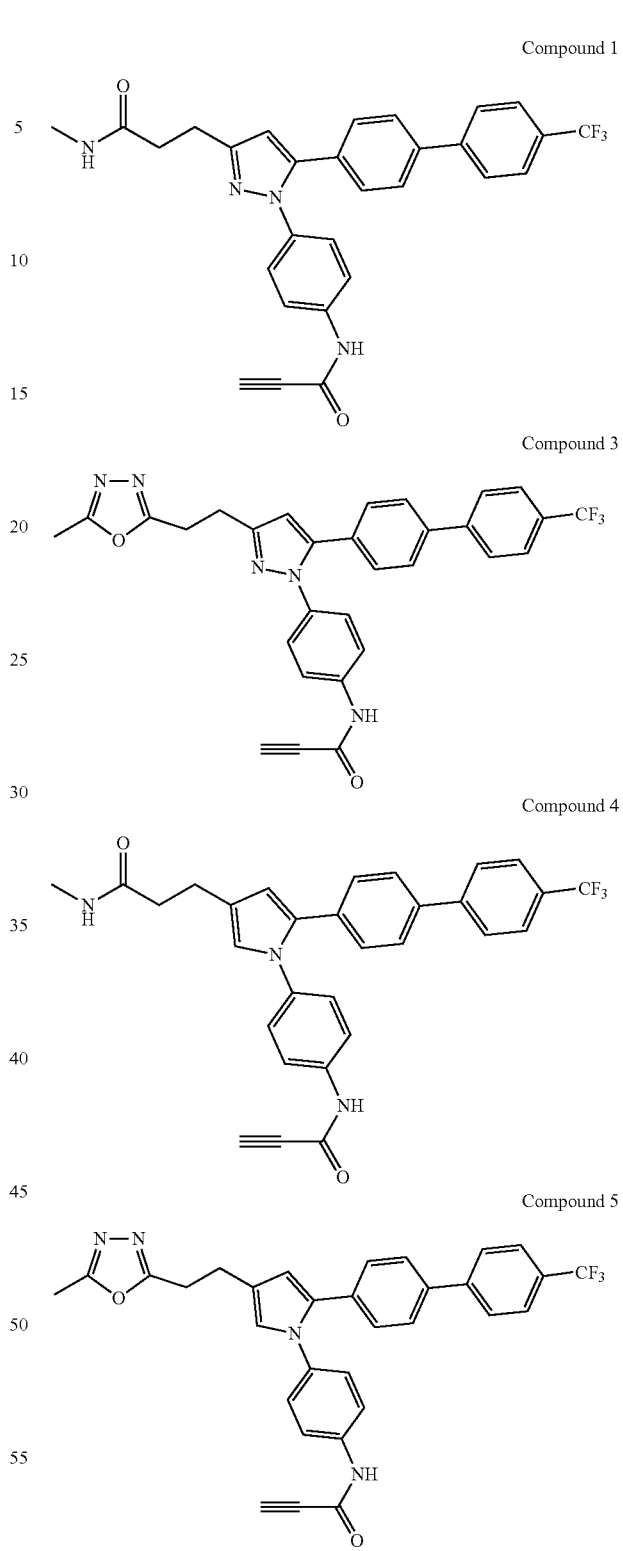

Thus according to this aspect of the invention there is provided a compound of the formula I, or a pharmaceutically acceptable for treating or inhibiting tumors According to an additional feature of this aspect of the invention there is provided a method of inducing an antitumor effect in a subject suffering from tumor comprising administering to the subject a pharmaceutical composition comprising an effective amount of compound of formula I or a pharmaceutically acceptable forms thereof.

In another aspect of the invention, preferably the anti-tumor effect is through inhibiting PKM2-mediated metabolic and nonmetabolic functions of cancer cells.

In one aspect of the invention, preferably, anti-tumor effect is selected from the group consisting of reducing tumor volume, inhibiting tumor growth, inhibiting tumor progression, altering metabolic activity in a tumor, inducing quiescence in a tumor, inhibiting or reducing tumor invasiveness, and reducing tumor weight.

In another aspect of the invention, preferably the tumor is comprising pancreatic cancer, breast cancer, oral cancer, colon cancer, prostate cancer, or lung cancer.

In one aspect of the invention, more preferably, the tumor is characterized with aggressive phenotype or drug-resistance, including, but not limited to triple-negative breast cancer, castration-resistant prostate cancer, oral cancer, colon cancer, EGFR mutant lung cancer, and pancreatic cancer.

In another aspect of the invention, the tumor is aggressive cancer and more preferably the aggressive cancer adopts glycolytic phenotype.

According the aspect of the invention, more preferably compounds of the invention are compounds 1 and 3-5 which have the following structures to be as an anti-tumor agent.

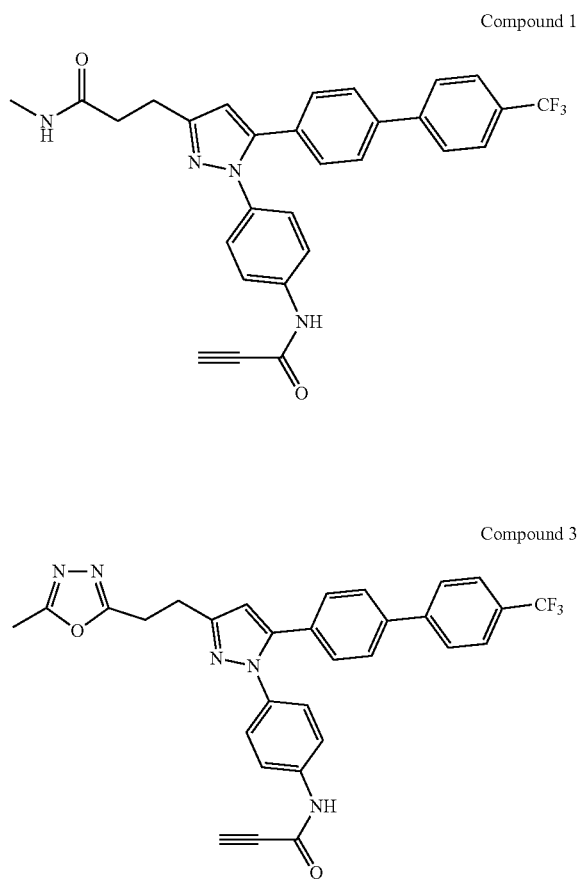

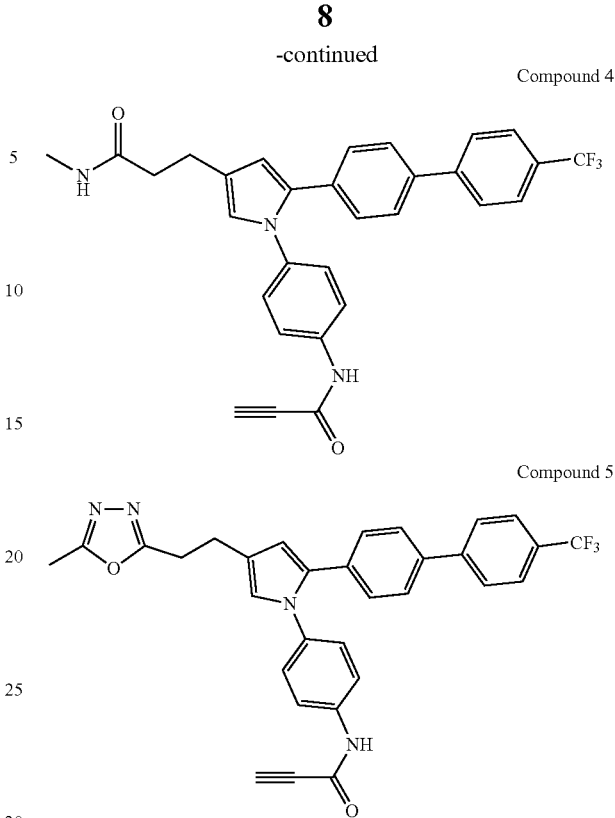

BRIEF DESCRIPTION OF THE DRAWINGS

FIG. 2. Exemplary synthetic scheme for compounds 1 and 2. (A) Structures of compound 22 versus compound 1 and its ABPP probe 2. (B and C) Synthetic schemes for compounds 1 (B) and 2 (C). Reaction conditions: (a) Pd(OAc)2 (2 mol %), K2CO3 (2 equiv), TBAB (1.3 equiv)/H2O, 60° C., 2 h; (b) TEA (1.5 equiv)/CH2C2; (c) MgBr·Et2O (2 equiv), DIPEA (2 equiv), rt, 20 h; (d) PTSA (1 equiv)/EtOH, 120° C., overnight; (f) BBr3/CH2Cl2, 0° C., rt, 90 min; (e) K2CO3/acetone, reflux, overnight; (h) SnCl2·H2O/EtOAc, reflux, 6-8 h; (i) TBTU/CH2Cl2, rt, 5 days.

FIG. 3. Differential antiproliferative effects of compounds 1 and 2 in different cancer cell lines by MTT assays. (A) Concentration-dependent suppressive effects of compound 1 on the viability of different cancer cell lines, including those of pancreas (Panc-1, AsPC-1, and MiaPaCa-2), breast (MDA-MB-231 and MCF-7), oral (SCC2095 and SCC4), and prostate (PC-3 and LNCaP). (B) Concentration-dependent suppressive effects of compounds 1 (left) and 2 (right) on the viability of lung cancer cell lines harboring mutant EGFR (H1650, PC-9, and H1975) versus those with wild-type EGFR (H460 and H157). Value, means±S.D. (n=6).

FIG. 5. Identification of PKM2 as a target of compound 1. (A) A list of kinase protein targets of compound 1 identified by LC-MS/MS in PC-9 cancer cells. (B) Protein-protein interaction pathway map of compound 1's target proteins. (C) GO functional annotation for related targets and biological processes of PKM2.

FIG. 7. Identification of Cys326 and Cys317 as potential compound 1 modified sites on PKM2 via MS/MS analysis. MS/MS spectra derived from compound 1-modified tryptic peptides of PKM2 afforded (A) the $[M+5H]^{5+}$ precursor ion at m/z 615.12323 Da for the Cys326-containing peptide AGKPVIC$^{326}$ATQMLESMIKKPRPTR and (B) the $[M+3H]^{3+}$ precursor ion at m/z 499.55002 Da for the Cys317-carrying peptide MMIGRC$^{317}$NR (B). The amino acid sequences and respective b and y ions are shown in each spectrum, with the compound 1-modified cysteine residues underlined. All detected b and y ions carrying the modified Cys residue (b7-11, b14, and y19-20 for peptide AGKPVIC$^{326}$ATQMLESMIKKPRPTR; b6, y3, and y5-7 for peptide MMIGRC$^{31}$NR) dotted in the peptide sequence shown were found to retain the compound 1 moiety (+516.1773 Da). (C) A depiction of the Cys326 and Cys317 residues on PKM2 (PDB:3 gr4).

FIG. 9. In vivo efficacy of compound 1 in suppressing the growth of PC-9 xenograft tumors in nude mice. (A) Suppressive effect of compound 1 at 10 mg/kg via daily i.p. injection on PC-9 xenograft tumor growth after 25 days of treatment. Top, representative images of vehicle- and compound 1-treated PC-9 xenograft tumor-bearing mice and dissected tumor samples after 25 days of treatment. Bottom, effects of compound 1 versus vehicle control on tumor volumes (left), tumor weight (right), and body weight (B) in the course of treatment. Data are expressed as mean±S.D. (n=8). *P<0.001. (C) Left, Western blot analysis of the effects of compound 1 versus vehicle control on the expression of PKM2 and downstream targets, including PGK1, EGFR, Stat3 and β-catenin in tumor lysates. GAPDH as an internal control. Right, quantification of the ratio of protein expression level was normalized to GAPDH of tumor lysate by ImageJ tool. P<0.01, ***P<0.001.

EXAMPLES

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.); Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der organischen Chemie, 4, Aufl. Ed. Springer-Verlag, Berlin, Germany, including supplements (also available via the Beilstein online database)).

Figure 1:
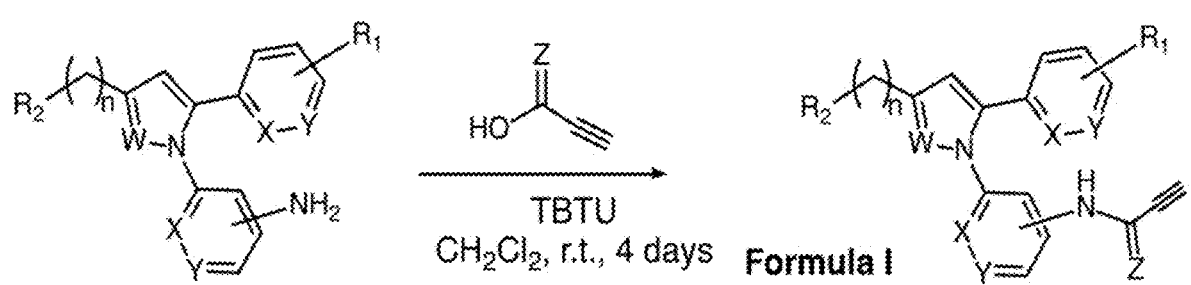
FIG. 1. Depicts the synthetic strategy for developing irreversible PKM2 inhibitors. The general chemical structure of the irreversible PKM2 inhibitor is showing as formula I.

FIG. 1 illustrates a general synthetic scheme for preparing propiolylamide-based irreversible PKM2 inhibitors of the present invention. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

Example 1. Procedure for the Synthesis of Compounds 1 and 2

In an effort to develop irreversible kinase inhibitors, we chose the core structures of several published kinase inhibitors to couple with a propiolyl moiety, which could act as an electrophilic warhead to irreversibly modify the cysteine residues of target proteins. Among various core structures evaluated, that of the integrin-linked kinase inhibitor compound 22 (FIG. 2A), i.e., 3-(1-(4-aminophenyl)-5-[4'-(trifluoromethyl)-(1,1'-biphenyl)-4-yl]-1H-pyrazol-3-yl)-N-methyl-propanamide (i, FIG. 2B), was of particular interest as the resulting propargylic amide 1 exhibited differential growth inhibition in a panel of cancer cell lines (FIG. 3A). When compound 1 was incubated with a stoichiometric amount of free cysteine in solution, mass spectral analysis showed the formation of a covalent 1-cysteine adduct, which provided a proof-of-concept that compound 1 undergoes Michael addition with a nucleophile.

To help identify the cellular target of compound 1, we developed a clickable ABPP probe of compound 1, N-(4-(5-(4'-(ethynyloxy)-[1,1'-biphenyl]-4-yl)-3-(3-(methylamino)-3-oxopropyl)-1H-pyrazol-1-yl)phenyl)propiolamide (compound 2; FIG. 2A), which contained a prop-2-yn-1-yloxy moiety, in lieu of $CF_3$, as a reporter tag at the terminal phenyl ring. This ABPP probe was used to conduct SILAC-based proteomic analysis. The alkyne reporter tag allowed the biotinylation of compound 2-labelled target proteins via Cu(I)-catalyzed biorthogonal conjugation with azide-biotin, which facilitated the subsequent streptavidin-bead pulldown to undergo proteomic analysis. The synthesis of compound 2 was depicted in the scheme shown in FIG. 2C.

Experimental Procedures

General 3-(1-(4-Aminophenyl)-5-(4'-(trifluoromethyl)-[1,1'-biphenyl]-4-yl)-1H-pyrazol-3-yl)-N-methylpropanamide (i) was prepared according to a published procedure (see *J Med Chem* 2011, 54, 6364-6374). All commercially available reagents were used without further purification unless otherwise stated. Anhydrous THF was obtained by distilling commercial THF over calcium hydride, and anhydrous DMF was obtained by distillation over $P_2O_5$ under reduced pressure. Silica gel for column chromatography was purchased from Fisher Scientific (230-400 mesh). Routine $^1H$ and C nuclear magnetic resonance spectra were recorded on a Bruker AV400 or AVII 500 spectrometer. Samples were dissolved in deuterated chloroform ($CDCl_3$) or dimethyl sulfoxide (DMSO-$d_6$) with tetramethylsilane (TMS) as a reference. Electrospray ionization mass spectrometry analyses were performed on a Bruker maXis 4G mass spectrometer. All biologically evaluated compounds were shown in exist in greater than 95% purity by the following methods. Purity of compound 1 was confirmed by HPLC, which was measured by Reverse Phase HPLC System Column: Merck 50995 Lichrospher 100 RP18, Column temperature (° C.): 20, Column length (mm): 250-4 mm endcapped, Column internal diameter (mm): 5, Detector: Jasco MD-910, Mobile Phase: MeOH:$H_2O$=80:20, Injection volume (μL): 20, Flow rate: 0.5 mL/min. Quantitative iD 1H NMR (qNMR) was conducted to confirm the purity of compound 2 by following Journal of Medicinal Chemistry's published guidelines (Purity by absolute qNMR: http://pubs.acs.org/paragonplus/submission/jmcmar/jmcmar_purity_instructions.pdf). The syntheses of compounds 1 and 2 were carried out according to the schemes depicted in FIG. 2, of which the details are described as follows.

N-(4-(3-(3-(Methylamino)-3-oxopropyl)-5-(4'-(trifluoromethyl)-[1,1'-biphenyl]-4-yl)-1H-pyrazol-1-yl)phenyl)propiolamide (1). To an ice-cold solution of intermediate i (92.8 mg, 0.2 mmol) in $CH_2Cl_2$ (4 mL) was added O-(benzotriazol-1-yl)-N,N,N',N'-tetramethyluronium tetrafluoroborate (TBTU) (257 mg, 0.8 mmol), followed by propynoic acid (61 μL, 1.0 mmol, 5.0 eq.). The reaction mixture was stirred at room temperature for 4-5 days under argon, and concentrated. The residue was purified by flash column chromatography to afford 69 mg (67%) of compound 1 as an off-white solid, of which the purity was determined to be of 97.97% by HPLC. $^1H$ NMR (500 MHz, $CDCl_3$) δ 8.01 (s, 1H), 7.91 (d, J=8.0 Hz, 2H), 7.73-7.62 (m, 8H), 7.47 (d, J=8.5 Hz, 2H), 6.56 (s, 1H), 5.51 (s, 1H), 3.05 (t, J=7.5 Hz, 2H), 2.94 (s, 1H), 2.79 (d, J=5.0 Hz, 3H), 2.47 (t, J=7.7 Hz, 2H). $^{13}C$ NMR (125 MHz, DMSO-$d_6$) δ 171.5, 150.2, 3, 150.2, 145.1, 144.2, 138.3, 138.1, 135.8, 133.7, 128.2, 127.8, 127.7, 126.3, 126.2, 126.1, 125.9, 123.8, 120.7, 103.4, 79.6, 78.8, 77.9, 34.4, 25.9, 22.4. HRMS (ESI): calcd. for $C_{29}H_{23}N_4O_2F_3Na$, $[M+Na]^+$ 539.1671 Da, found 539.1672 Da.

N-(4-(3-(3-(methylamino)-3-oxopropyl)-5-(4'-(prop-2-yn-1-yloxy)-[1,1'-biphenyl]-4-yl)-1H-pyrazol-1-yl)phenyl) propiolamide (2) was synthesized as follows (FIG. 2C).

1-(4'-Methoxy-[1,1'-biphenyl]-4-yl)ethan-1-one (ii) (FIG. 2C, step a). 4-Methoxy phenylboronic acid (3.0 g, 19.7 mmol) was added to a solution of 4-bromo-acetophenone (4.3 g, 21.7 mmol), palladium (II) acetate (88 mg, 2 mol %), potassium carbonate (8.15 μg, 59.1 μmmol), and tetrabutylammonium bromide (TBAB; 8.25 g, 25.6 mmol). To the reaction mixture was added water (200 mL), heated to 60° C. with stirring under argon for 2 hours, cooled, diluted with water, and extracted with ethyl acetate. The organic layer was dried and concentrated, and the residue was purified by flash column chromatography (ethyl acetate:hexane, 3:7) to afford ii (4.0 g, 90% yield). $^1H$ NMR (500 MHz, $CDCl_3$) δ 8.07 (d, J=8.5 Hz, 2H). 7.64 (d, J=8.0 Hz, 2H), 7.57 (d, J=9.0 Hz, 2H), 7.00 (d, J=8.5 Hz, 2H), 3.86 (s, 3H), 2.62 (s, 3H). $^{13}C$ NMR (125 MHz, $CDCl_3$) δ 197.7, 159.9, 145.4, 135.3, 132.3, 128.9, 128.4, 126.6, 114.4, 55.4, 26.6. HRMS (EI): calcd for $C_5H_4O_2$, $[M]^+$ 226.0994 Da, found 226.0992 Da.

Ethyl 4-(1H-benzo[d][1,2,3]triazol-1-yl)-4-oxobutanoate (iii) (step b). To an ice-cooled solution of benzotriazole (10 g, 84 mmol) and triethylamine (17.6 mL, 126 mmol) in dichloromethane (DCM; 200 mL) was added ethyl-4-chloro-4-oxobutyrate (13.8 g, 84 mmol) slowly. The resulting mixture was brought to room temperature, and stirred for overnight. Observed white salt was filtered off, and washed with 2 N HCl (2×200 mL), followed by brine (200 mL). Organic layer was dried over $Na_2SO_4$, concentrated, and dried under vacuum to give compound iii, which was used directly for the next step without purification.

Ethyl (Z)-4-hydroxy-6-(4'-methoxy-[1,1'-biphenyl]-4-yl)-6-oxohex-4-enoate (iv)(step c). To a solution of compound ii (3.0 g, 13.25 mmol) in dry DCM (150 mL) was added compound iii (3.9 g, 15.9 mmol) and magnesium bromide ethyletherate (6.8 g, 26.5 mmol) under argon. The resulting solution was stirred under argon for 10 min, added dropwise N,N-diisopropylethylamine (DIPEA; 4.6 mL, 26.5 mmol), stirred for 16 hours, and washed, in tandem, with 10% 2 N HCl (150 mL×1) and water (200 mL×2). The organic phase was dried and concentrated. The residue was purified by chromatography (ethyl acetate:hexane, 9:1), followed by recrystallization in ethanol to give compound iv (3.2 g, 68% yield). $^1H$ NMR (500 MHz, CDCl3) δ 7.91 (d, J=8.5 Hz, 2H). 7.63 (d, J=8.5 Hz, 2H), 7.57 (d, J=8.5 Hz, 2H), 7.00 (d, J=9.0 Hz, 2H), 6.23 (s, 1H), 4.17 (q, J=7.0 Hz, 2H), 3.86 (s, 3H), 2.82 (t, J=7.0 Hz, 2H), 2.70 (t, J=7.0 Hz, 2H), 1.27 (t, J=7.0 Hz, 3H). $^{13}C$ NMR (125 MHz, CDCl3) δ 196.6, 180.4, 172.6, 159.9, 144.6, 132.4, 132.3, 128.4, 128.3, 127.4, 126.8, 126.7, 114.4, 96.0, 60.7, 55.4, 34.5, 29.2, 14.2. HRMS (ESI): calcd. for $C_{21}H_{22}O_5Na$, $[M+Na]^+$ 377.1365 Da, found 377.1356 Da.

Ethyl 3-(5-(4'-methoxy-[1,1'-biphenyl]-4-yl)-1-(4-nitrophenyl)-1H-pyrazol-3-yl) propanoate (v) (step d). To a solution of compound iv (3.0 g, 8.5 mmol) in ethanol (40 mL) was added 4-nitro-phenylhydrazine hydrochloride (1.92 g, 10.2 mmol) and p-toluenesulfonic acid (PTSA; 1.6 g, 8.5 mmol). The resulting solution was heated to reflux with stirring for overnight, cooled to room temperature, filtered and washed with ethanol to give compound v as yellow crystal (3.0 g, 75% yield). $^1$H NMR (500 MHz, CDCl$_3$) δ 8.37 (d, J=9.0 Hz, 2H). 7.88 (d, J=8.0 Hz, 2H), 7.78 (d, J=9.0 Hz, 2H), 7.61 (d, J=8.0 Hz, 2H), 7.57 (d, J=8.5 Hz, 2H), 6.99 (d, J=8.5 Hz, 2H), 6.34 (s, 1H), 4.15 (q, J=7.0 Hz, 2H), 3.86 (s, 3H), 3.13 (t, J=7.5 Hz, 2H), 2.74 (t, J=7.5 Hz, 2H), 1.25 (t, J=7.0 Hz, 3H). $^{13}$C NMR (125 MHz, CDCl3) δ 171.7, 159.3, 152.7, 146.3, 143.7, 140.8, 133.1, 130.7, 128.0, 126.9, 126.2, 124.8, 114.3, 104.6, 60.9, 55.4, 33.1, 22.2, 14.2. HRMS (EI): calcd for $C_{27}H_{25}N_3O$, $[M]^+$ 471.1794 Da, found 471.1801 Da.

3-(5-(4'-Methoxy-[1,1'-biphenyl]-4-yl)-1-(4-nitrophenyl)-1H-pyrazol-3-yl)-N-methyl-propanamide (vi)(step e). To a solution of compound v (3.0 g) in ethanol (15 mL) was added 1 M methylamine in ethanol solution (10 mL). The resulting solution was heated to 120° C. with stirring in a sealed tube for 16 hours and concentrated, followed by recrystallization in ethanol to give compound vi as yellow powder (2 g, 69%). $^1$H NMR (400 MHz, DMSO-d$_6$) δ 8.40 (d, J=8.4 Hz, 2H). 8.13 (s, 1H), 7.96~7.90 (m, 4H), 7.71~7.65 (m, 4H), 7.03 (d, J=8.0 Hz, 2H), 6.95 (s, 1H), 3.80 (s, 3H), 3.07 (t, J=7.2 Hz, 2H), 2.56 (bs, 5H). $^{13}$C NMR (100 MHz, DMSO-d6) δ 171.5, 159.5, 151.9, 146.2, 145.8, 144.9, 140.0, 132.4, 131.2, 128.1, 126.9, 126.4, 125.3, 125.2, 114.8, 105.1, 55.7, 34.1, 25.9, 22.9. HRMS (ESI-negative): calcd. for $C_{26}H_{23}N_4O_4$, $[M-H]^-$ 455.1719 Da, found 455.1714 Da.

3-(5-(4'-Hydroxy-[1,1'-biphenyl]-4-yl)-1-(4-nitrophenyl)-1H-pyrazol-3-yl)-N-methyl propanamide (vii) (step f). BBr$_3$ (1.0 M in DCM], 17.52 mL, 17.52 mmol) was added dropwise into ice cold mixture of compound vi (2 g, 4.38 mmol) in DCM (25 mL). After stirring the mixture at room temperature for 90 min, progress of reaction was monitored by TLC. After the complete consumption of compound v, the mixture was cooled to 0° C., and then added ice water slowly. The resulting yellow solid was filtered and washed with DCM, followed by ethyl acetate to obtain pure compound vii (1.2 g, 62%). $^1$H NMR (500 MHz, DMSO-d$_6$) δ 9.68 (s, 1H), 8.41 (d, J=9.2 Hz, 2H). 7.95 (d, J=8.8 Hz, 2H), 7.89 (d, J=8.4 Hz, 2H), 7.87 (d, J=8.0 Hz, 2H), 7.67 (d, J=8.0 Hz, 2H), 7.55 (d, J=8.4 Hz, 2H), 6.91 (s, 1H), 6.87 (d, J=8.8 Hz, 2H), 3.07 (t, J=7.6 Hz, 2H), 2.57 (d, J=4.8 Hz, 3H), 2.53 (t, J=7.6 Hz, 2H). $^{13}$C NMR (100 MHz, DMSO-d$_6$) δ 171.3, 157.7, 151.9, 146.1, 145.7, 144.8, 140.3, 130.7, 130.6, 127.9, 126.5, 126.2, 125.2, 125.1, 116.1, 104.9, 34.0, 25.8, 22.7. HRMS (ESI-negative): calcd for $C_{25}H_{21}N_4O_4$, $[M-H]^-$ 441.1563 Da, found 441.1563 Da.

N-Methyl-3-(1-(4-nitrophenyl)-5-(4'-(prop-2-yn-1-yloxy)-[1,1'-biphenyl]-4-yl)-1H-pyrazol-3-yl)propanamide (viii) (step g). To a solution of compound vii (1.2 g, 2.7 mmol) in acetone (150 mL) was added K$_2$CO$_3$ (748 mg, 5.4 mmol), followed by propargyl bromide (80% solution in toluene; 0.86 mL, 5.4 mmol). The resulting mixture was refluxed for 24 hours, cooled to room temperature, and concentrated under reduced pressure. To the residue was added water, followed by sonication, and the resulting yellow solid was filtered off, washed several times with water, and dried to obtain compound viii (1.2 g, 92% yield). $^1$H NMR (500 MHz, CDCl$_3$) δ 8.38 (d, J=9.0 Hz, 2H). 7.88 (d, J=8.0 Hz, 2H), 7.80 (d, J=8.5 Hz, 2H), 7.61 (d, J=8.0 Hz, 2H), 8.58 (d, J=8.5 Hz, 2H), 7.07 (d, J=8.5 Hz, 2H), 6.62 (s, 1H), 5.45 (s, 1H), 4.75 (d, J=1.5 Hz, 2H), 3.19 (t, J=7.5 Hz, 2H), 2.83 (d, J=5.0 Hz, 3H), 2.57 (t, J=7.5 Hz, 2H), 2.55 (s, 1H). HRMS (ESI-negative): calcd for $C_{28}H_{23}N_4O_4$, $[M-H]^-$ 479.1719 Da, found 479.1717 Da.

3-(1-(4-Aminophenyl)-5-(4'-(prop-2-yn-1-yloxy)-[1,1'-biphenyl]-4-yl)-1H-pyrazol-3-yl)-N-methylpropanamide (ix) (step h). To a solution of compound viii (1.2 g, 2.5 mmol) in ethyl acetate (60 mL) was added SnCl$_2$·H$_2$O (3.38 g, 14.98 mmol) under argon. The resulting mixture was heated to reflux with stirring under argon for 6-8 hours, and cooled to room temperature. The reaction mixture was diluted with ethyl acetate, and washed with a saturated solution of NaHCO$_3$. The aqueous layer was extracted with ethyl acetate, and combined with the organic layer. The combined solution was dried over Na$_2$SO$_4$, filtered, and concentrated to get pure compound ix (1.1 g, 97% yield). $^1$H NMR (400 MHz, CDCl$_3$) δ 7.87 (d, J=8.4 Hz, 2H). 7.58 (d, J=8.4 Hz, 4H), 7.24 (d, J=10.4 Hz, 2H), 7.05 (d, J=8.8 Hz, 2H), 6.74 (d, J=8.4 Hz, 2H), 6.51 (s, 1H), 5.42 (s, 1H), 4.74 (d, J=2.4 Hz, 2H), 3.00 (t, J=7.6 Hz, 2H), 2.79 (d, J=5.2 Hz, 3H), 2.54 (t, J=2.4 Hz, 1H), 2.44 (t, J=7.8 Hz, 2H).

N-(4-(3-(3-(Methylamino)-3-oxopropyl)-5-(4'-(prop-2-yn-1-yloxy)-[1,1'-biphenyl]-4-yl)-1H-pyrazol-1-yl)phenyl) propiolamide (2) (step i). To an ice-cold solution of compound (1.1 g, 2.44 mmol) in DCM (20 mL) was added TBTU (3.1 g, 9.76 mmol) followed by propynoic acid (855 mg, 12.20 mmol). The reaction mixture was stirred at room temperature for 4-5 days under argon and concentrated under reduced pressure. The residue was purified by flash column chromatography to afford 150 mg of compound 2 as an off-white solid of which the purity was determined to be of 97.3% by qNMR. $^1$H NMR (500 MHz, DMSO-d$_6$) δ 11.04 (s, 1H), 7.86 (d, J=8.5 Hz, 3H), 7.77 (d, J=8.5 Hz, 2H), 7.68 (t, J=8.5 Hz 4H), 7.54 (d, J=9.0 Hz, 2H), 7.08 (d, J=8.5 Hz, 2H), 6.76 (s, 1H), 4.85 (d, J=2.5 Hz, 2H), 4.48 (s, 1H), 3.59 (t, J=2.0 Hz, 1H), 2.90 (t, J=7.5 Hz, 2H), 2.55 (d, J=4.5 Hz, 3H), 2.45 (t, J=7.5 Hz, 2H). $^{13}$C NMR (125 MHz, DMSO-d$_6$) δ 171.0, 156.9, 149.9, 149.7, 144.4, 138.9, 137.7, 135.3, 132.8, 131.5, 127.5, 126.4, 125.7, 125.6, 120.1, 115.3, 102.7, 79.2, 78.3, 77.5, 55.5, 33.8, 25.5, 21.9. HRMS (ESI): calcd for $C_{31}H2N_4O_3Na$, $[M+Na]^+$525.1903 Da, found 525.1902 Da.

Example 2. Compounds 1 and 2 Shows Differential Antiproliferative Efficacies Against Cancer Cell Lines with Different Genetic Characteristics The antitumor activity of compound 1 was evaluated in a panel of cancer cell lines from different tissue types, including those of pancreas (Panc-1, AsPC-1, MiaPaCa-2), breast (MDA-MB-231, MCF-7), oral (SCC2095, SCC4), prostate (PC-3, LNCaP), and lung (H1650, PC-9, H1975, H460, H157). MTT assays indicate that these cell lines exhibited differential susceptibility to compound 1 with IC$_{50}$ values ranging from 0.1 μM (MDA-MB-231) to >2 μM (LNCaP and H157), which could be attributable to differences in their genetic characteristics (FIG. 3). For example, the aggressive MDA-MB-231 and PC-3 cells were more susceptible to compound 1-mediated growth inhibition relative to their non-invasive counterparts MCF-7 (IC$_{50}$, 0.1 versus 1 μM) and LNCaP cells (IC$_{50}$, 0.6 versus >2 μM), respectively. This differential sensitivity was also evident in lung cancer cell lines as mutant EGFR cell lines (IC$_{50}$, H1650, 0.2 μM; PC-9, 0.5 μM; H1975, 1 μM) were more sensitive as compared to those harboring wild type EGFR (IC$_{50}$, H460, 1.5 μM; H157, >2 μM) (FIG. 3B, left). Similar findings were also noted among these lung cancer cell lines in response to compound 2 treatments (FIG. 3B, right). This discriminative antiproliferative effect suggested a unique cellular target and/or pathway by which compound 1 mediated its antitumor activity.

Consistent with the role of PKM2 in promoting tumor growth and invasion, the ability of compound 1 to preferentially suppress the proliferation of cancer cell lines with more aggressive phenotype within the same tissue type is noteworthy (e.g., MDA-MB-231 versus MCF-7, PC-3 versus LNCaP, and EGFR mutant versus wild-type lung cancer cells). It is well documented that aggressive cancer cells adopt glycolytic phenotype to gain growth advantage in face of adverse environments, and are more relying upon glycolysis for survival. Thus, glycolytic versus nonglycolytic phenotype, instead of the expression level of PKM2, might underlie the differential susceptibility to the antiproliferative activity of compound 1 between aggressive and noninvasive cancer cell lines.

To shed light onto its potential target, compound 1 was submitted to a commercial vendor for kinase profiling analysis (Life Technologies' SelectScreen Profiling Service), in which the inhibitory effects of compound 1 at 500 nM on the activity of 246 different kinases as well as substrate binding to 143 different kinases were tested. However, the results indicate that none of the kinases examined was effectively inhibited by compound 1 which argued against the involvement of these kinases in the tumor-suppressive effect of compound Experimental Procedures Cell lines, cell culture, biochemical reagents, and antibodies. MiaPaCa-2, AsPC-1, and Panc-1 human pancreatic cancer cells, MCF-7 and MDA-MB-231 breast cancer cells, SCC4 and SCC2059 oral cancer cells, PC-3 and LNCaP prostate cancer cells, H157, H460, H1975, PC-9 and H1650 lung cancer cells were obtained from the American Type Culture Collection (ATCC, Manassas, Va.). All these cells were maintained in recommended growth medium (RPMI 1640 or DMEM) supplemented with 10% fetal bovine serum (FBS) (Invitrogen, Carlsbad, Calif., USA) and antibiotics at 37° C. in a humidified incubator containing 5% $CO_2$. For SILAC experiments, PC-9 cells were grown in SILAC DMEM medium (Thermo Fisher) supplemented with 10% dialyzed FBS and 100 µg/mL each of unlabeled L-arginine and L-lysine (light medium) or $^{13}C/^{15}N$ stable isotope-labeled L-arginine and L-lysine (heavy medium). PC-9 cells were passaged at least six times in isotope-containing DMEM medium before being used for analysis by LC-MS/MS.

Cell viability assays. Drug effects on cell viability was assessed by 3-(4,5-dimethylthiazol-2-yl)-2,5-diphenyltetrazolium bromide (MT) assays. Cancer cells were seeded onto 96-well plates at a density of 3,500 cells per well in the presence of 10% FBS. After overnight incubation, cells were exposed to test agents vis-A-vis vehicle in the presence of 5% FBS for 24 hours. After treatment, cells were incubated with MTT (Biomatik, Wilmington, Del.) for an additional 1 hour. The medium was then removed from each well and replaced with DMSO to dissolve the reduced MTT dye for subsequent colorimetric measurement of absorbance at 560 nm. Cell viabilities are expressed as percentages of viable cells relative to the corresponding vehicle-treated control group.

Example 3. Identification of PKM2 as a Target of Compound 1 Via ABPP—SILAC

Figure 4:
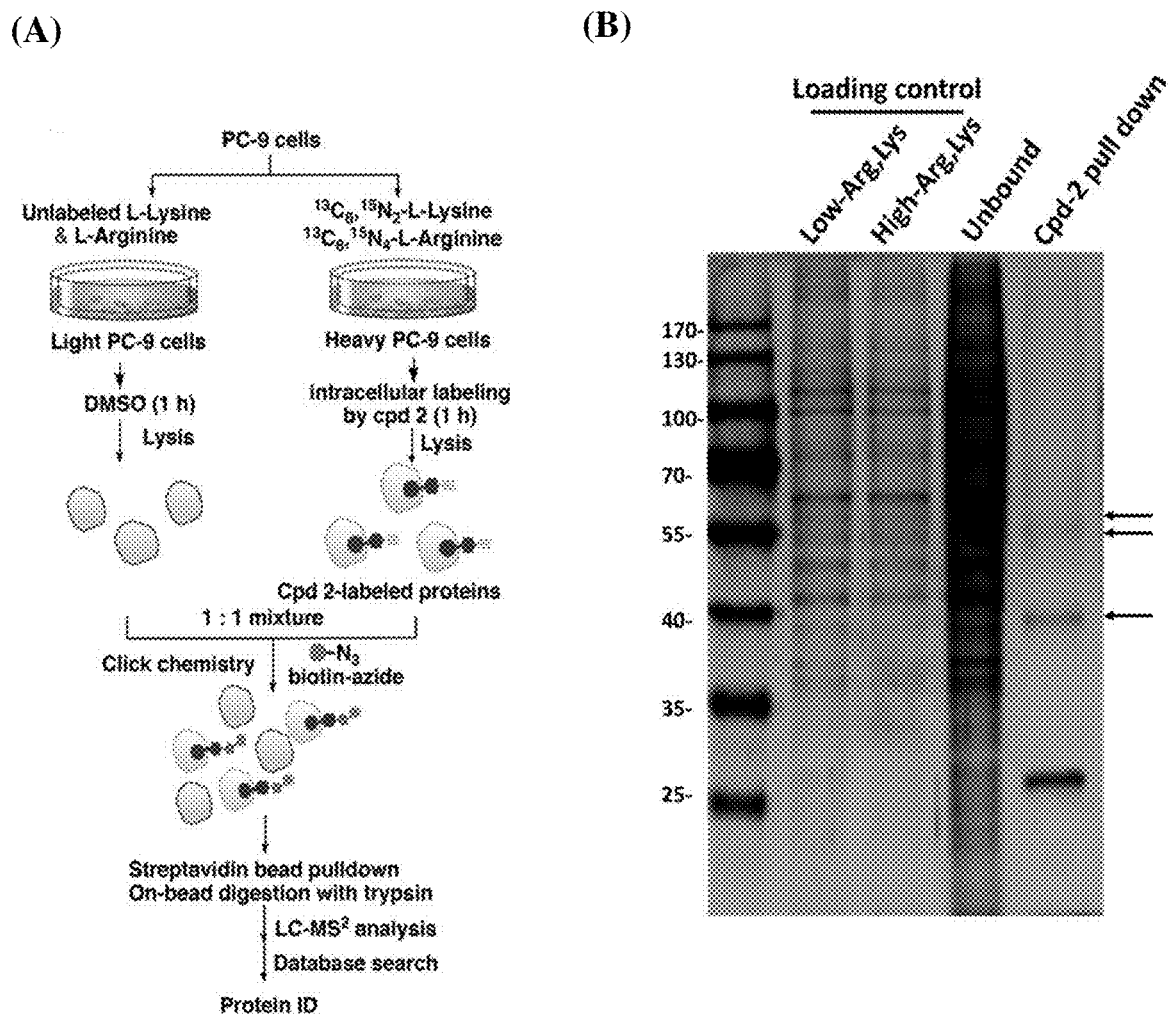
FIG. 4. ABPP—SILAC-based proteomic analysis to identify cellular targets of compound 1. (A) A schematic diagram depicting the ABPP—SILAC-based quantitative proteomics strategy. (B) SDS-PAGE analysis of ABPP-labelled target proteins via streptavidin-bead pulldown, which was silver stained. The indicated gel regions were excised from SDS-PAGE gels.

As part of our effort to identify compound 1's target(s), we embarked on the use of compound 2 as an ABPP probe to conduct SILAC-based proteomic analysis. Compound 2 exhibited a pattern of growth inhibition similar to that of compound 1 among different lung cancer cell lines examined. As PC-9 cells showed the highest sensitivity to both compounds, we used this cell line to conduct target identification via ABPP—SILAC, as depicted in FIG. 4A. In this experiment, PC-9 cells were grown in cultural medium supplemented with unlabeled L-arginine and L-lysine (light medium) versus $^{13}C/^{15}N$ stable isotope-labeled L-arginine and L-lysine (heavy medium), generating two populations of cells (light versus heavy cells). Heavy PC-9 cells were then exposed to the ABPP (1 µM) for 1 hour to allow intracellular labelling of target proteins, while light cells were treated with DMSO vehicle under the same condition. These light and heavy cells were mixed at a 1:1 ratio and lysed, and cell lysates were treated with biotin-azide to facilitate the biotinylation of compound 2-labelled target proteins. Subsequently, the resulting biotin conjugates of ABPP-labelled target proteins were purified by streptavidin bead pulldown, followed by 10% SDS-PAGE. Silver staining of the gel showed three protein bands at approximately 45, 58, and 73 kDa, respectively (arrowhead, FIG. 4B), each of which was excised from the gel and subjected to in-gel trypsin digestion. These peptide mixtures were analyzed by liquid chromatography-tandem mass spectrometry (LC-MS/MS), and the resulting data were searched against various primary sequence databases by using the Mascot search engine. This proteomic analysis led to the identification of nine putative protein targets, including PKM2, lactate dehydrogenase A (LDHA), citrate synthase (CS), malate dehydrogenase (MDHM), ATP-citrate lyase (ACYL), α-enolase (ENOA), phosphoenolpyruvate carboxylase (PCKGM), acyl-CoA synthetase family member 3 (ACSF3), and phosphoglycerate kinase (PGK1), among which the protein with the highest matching score was the 58 kDa PKM2 (FIG. 5A). Analysis using the STRING database revealed the protein association network of PKM2 with other identified target proteins (except ACSF3) through direct or indirect interactions, of which the map is depicted in FIG. 5B. Additionally, to shed light onto cellular changes in response to compound 2, these target proteins were functionally categorized according to the Gene Ontology analysis for biological processes. As shown, these proteins were intimately involved in the metabolic processes of glucose, NAD, and citrate (FIG. 5C), indicating the ability of compound 2 to target energy metabolism in PC-9 cells.

Experimental Procedures

SILAC analysis and click chemistry. PC-9 cells ($2\times10^6$ cells/plate) were seeded in SILAC DMEM growth medium containing unlabeled L-arginine and L-lysine (light medium) or $^{13}C/^{15}N$ stable isotope-labeled L-arginine and L-lysine (heavy medium) in 10-cm plates. After 16 hours, the SILAC DMEM medium was aspirated off, and cells were washed twice with Dulbecco's phosphate-buffered saline (DPBS), followed by the addition of, in tandem, fresh DMEM medium and compound 1 (µM) or DMSO. After incubation at 37° C. for 1 hour, cells were collected, washed three times with DPBS, suspended in cold DPBS containing a protease inhibitor cocktail (Roche), and lysed by a probe sonicator, followed by centrifugation at 100,000 g for 30 min. The supernatant was transferred to a 1.5 mL microfuge tube, and the protein concentration was determined by the BCA protein assay (Thermo Fisher Scientific) and then normalized to 1 mg/mL. Heavy and light cell lysates at 500 µg each were mixed, and the combined cell lysates were subjected to the cupper-catalyzed Click reaction for 1 hour with 40 µM biotin-azide (PEG4 carboxamide-6-azidohexanyl biotin) using the Click-IT protein reaction buffer kit (Invitrogen) according to the manufacturer's instruction. Biotin-tagged proteins were then treated with 50 L of streptavidin-coupled magnetic beads (Dynabeads M-280 Streptavidin, Invitrogen) for 16 hours at 4° C. After incubation, cell lysates were washed by PBS containing 0.5% SDS three times to remove nonspecific binding. After wash, the streptavidin-coupled magnetic beads were incubated in 30 μL of 2× loading buffer for 10 min at 100° C. to separate out the targeted proteins from beads. The pulled-down proteins were subjected to 10% SDS-PAGE, and then stained with sliver staining before processing for LC-MS/MS.

Proteomic data analysis. Putative target proteins of compound 1 and protein-protein interaction network were identified and analyzed, respectively, through a web-based search of the STRING database (https://string-db.org/). The PKM2 interaction protein network was functionally characterized by using the Gene Ontology analysis for biological processes.

Example 4. Evidence that Compound 1 is an Irreversible Inhibitor of PKM2

Figure 6:
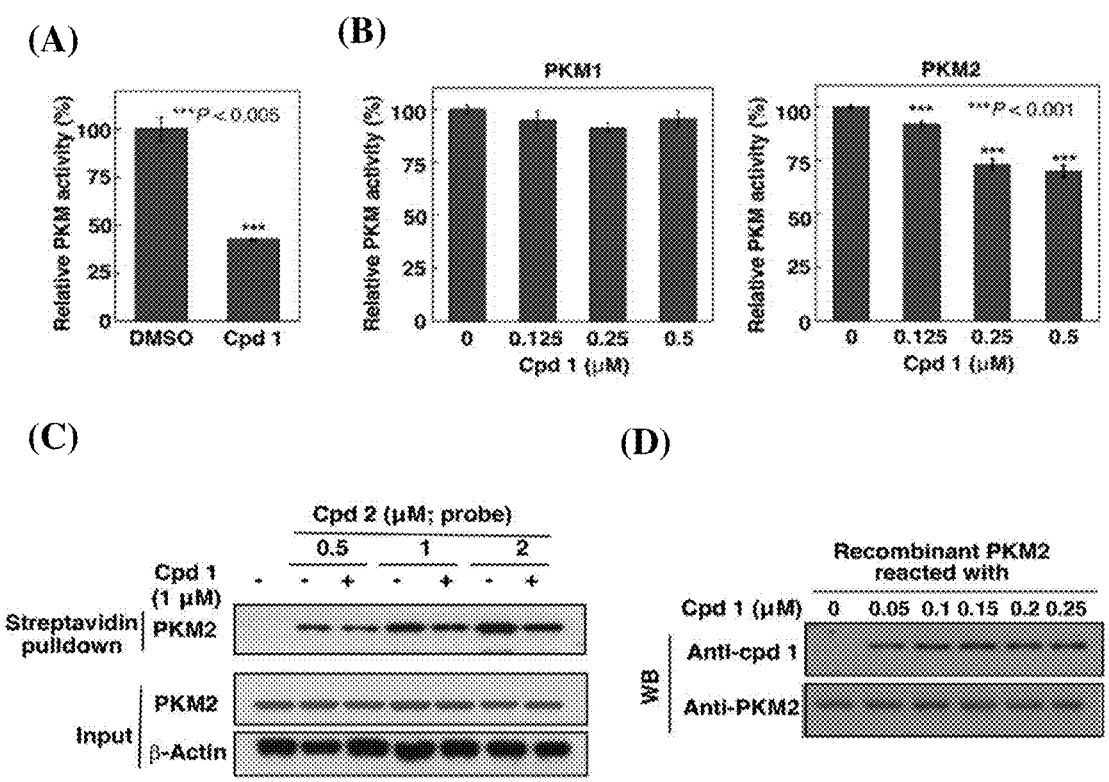
FIG. 6. Evidence that compound 1 is an irreversible inhibitor of PKM2. (A) PC-9 cells treated with compound 1 (0.25 µM) showed significantly reduced pyruvate kinase activity relative to vehicle control. Bar, means±S.D. (n=3). *P<0.005. (B) Compound 1 selectively inhibited the kinase activity of recombinant PKM2, but not recombinant PKM1. Bar, means±S.D. (n=3). *P<0.001. (C) Compound 1 was effective in competing with the ABPP probe compound 2 for PKM2 binding. PC-9 cells were pre-incubated with 1 µM compound 1 for 1 hour, and treated with compound 2 at indicated concentrations. Cells were lysed, and treated with biotin-azide, followed by streptavidin bead pulldown and Western blot analysis. (D) Anti-compound 1 antibodies cross reacted with compound 1-treated PKM2. Recombinant PKM2 (4 µg) was incubated with vehicle control or compound 1 at indicated concentrations at 4° C. for 6 hours, followed by immunoblotting with anti-PKM2 and anti-compound 1 antibodies.

The above ABPP—SILAC analysis suggests that PKM2 might represent a primary target for compound 1. This premise was supported by the significantly reduced pyruvate kinase activity (P<0.005) in PC-9 cells treated with compound 1 (0.25 μM) relative to that of vehicle control (FIG. 6A). As this cell-based kinase assay could not rule out the involvement of PKM1, we examined the abilities of compound 1 to inhibit the kinase activity of recombinant PKM2 (SAE0021, Sigma-Aldrich) versus recombinant PKM1 (SRP0415, Sigma-Aldrich) using a commercial PKM assay kit. As shown, after 20 min of exposure, compound 1 could suppress the kinase activity of PKM2 (P<0.001), while no appreciable inhibition was noted with PKM1 (FIG. 6B), indicating the specificity of compound 1 in PKM2 inhibition. In addition, we demonstrated that compound 1 was able to compete with the ABPP probe compound 2 for PKM2 binding. In brief, PC-9 cells were exposed to different concentrations of compound 2 in the presence of compound 1 (1 μM) for 1 hour, lysed, and the cell lysates were treated with biotin-azide, followed by streptavidin bead pulldown under the aforementioned conditions. Western blot analysis indicated that the binding of the ABPP probe to PKM2 was attenuated by compound 1 (FIG. 6C). Equally important, we raised antibodies against compound 1 to demonstrate the ability of compound 1 to form covalent adducts with recombinant PKM2. The antigen of compound 1 was prepared by coupling this small molecule with cysteine residues of ovalbumin, which was then used for immunization in guinea pigs. Consistent with the covalent mode of binding, Western blot analysis showed that these antibodies cross reacted with compound 1-treated PKM2 (FIG. 6D).

Experimental Procedures

Gel-based ABPP. PC-9 cells ($2\times10^6$) were seeded in DMEM growth medium in 10-cm plates. After overnight incubation, the growth medium was replaced with fresh medium, followed by the addition of 1 μM compound 1 or DMSO control. After 1 hour, the ABPP probe compound 2 at 0.5, 1 and 2 μM was then added, and incubated at 37° C. for an additional 1 hour. The cell lysates were subjected to copper-catalyzed Click reaction, and biotin-tagged proteins were treated with 50 μL of streptavidin-coupled magnetic beads for 16 hours at 4° C. After incubation, cell lysates were washed by PBS containing 0.5% SDS three times to remove nonspecific binding. After wash, the streptavidin-coupled magnetic beads were incubated in 30 μL of 2× loading blue for 10 min at 100° C. to separate out bound proteins from beads, which were then subjected to 10% SDS-PAGE.

Preparation of anti-compound 1 antiserum. compound 1 was coupled to the cysteine thiolate in ovalbumin (OVA) via the propiolyl moiety under alkaline conditions by using the modifications to a published method. In brief, two mL of OVA at 2 mg/mL in phosphate-buffered saline (PBS) was treated with 50 mM 1,4-dithioerytreitol at 37° C. for 1 hour, followed by the addition of, in tandem, 2 mL of 20% trichloroacetic acid and 20 mL of ice-cold acetone. The mixture was kept at −20° C. overnight, and the resulting precipitate was collected by low-speed centrifugation, and was dissolved in 2 mL of 8 M urea in 0.1 M sodium carbonate buffer, pH 9.4, containing 4 mg of compound 1. The solution was incubated at 37° C. for 4 hours and buffer-exchanged into PBS by centrifugal concentration using an Amicon device with a cutoff of 10 kDa (MilliporeSigma, Burlington, Mass., USA), and was then used for routine subcutaneous immunizations in guinea pigs. Following six biweekly injections, whole blood was collected from the anesthetized animals 10 days after the final injection.

Pyruvate kinase activity assays. PC-9 cells were seeded into 6 cm dishes at a concentration of $5\times10^5$ cells/mL. After 24 hours, cells were treated with 0.25 μM compound 1 or DMSO for 6 hours. The pyruvate kinase activity of compound 1-treated PC-9 and vehicle control cells was measured by using a commercial colorimetric assay kit from BioVision (Milpitas, Calif., USA) according to the manufacturer's protocol. In addition, to verify the specificity of compound 1 toward PKM2 versus PKM1, the inhibition of the kinase activity of recombinant PKM1 (SRP0415, Sigma-Aldrich) and recombinant PKM2 (SAE0021, Sigma-Aldrich) by compound 1 was conducted using the aforementioned assay kit.

Example 5. Mass Spectral Identification of Potential Compound 1-Modified Sites on PKM2

As PKM2 has a total of 10 cysteine residues (NCBI reference sequence: NM_002654), we conducted proteomic analysis to identify which cysteine residues were covalently modified by compound 1. Recombinant PKM2, prepared in our laboratory, was treated with compound 1, followed by tryptic digestion. To facilitate a more accurate and comprehensive mapping of the modified sites, in-solution digested compound 1-modified tryptic peptides of PKM2, obtained from 6 separate experiments were pooled and subjected to 48 repeated runs of nanoLC-MS/MS analysis under a data-dependent acquisition mode. The resulting MS/MS datasets were individually searched against the PKM2 human protein sequence (UniProtKB, P14618-1) database using the Mascot search engine. The search results from 48 analyses provided a protein sequence coverage of 97.1%. The corresponding MS/MS spectra for each of the compound 1-modified sites were then manually verified and annotated for the sequence informative b and y fragment ions. These MS/MS data afforded the $[M+5H]^{5+}$ quintuply protonated precursor ion at m/z 615.12323 for the Cys326-containing peptide (320-342) AGKPVIC$^{326}$ATQMLESMIKKPRPTR (FIG. 7A) and the $[M+3H]^{3+}$ triply charged precursor ion at m/z 499.55002 for the Cys317-carrying peptide (312-319) MMIGRC$^{317}$NR (FIG. 7B). In general, the modification site assignment was considered reliable if the b and y ions flanking the implicated site could be detected, with mass shifts corresponding to a compound 1-modified cysteine (+516.1773 Da). As expected, detected b and y ions carrying the modified Cys residue including b7-11, b14, and y19-20 for peptide AGKPVIC$^{326}$ATQMLESMIKKPRPTR; b6, y3, and y5-7 for peptide MMIGRC$^{317}$NR (dotted in the peptide sequence shown) were found to retain the compound 1 moiety. Together, this proteomic analysis revealed that compound 1 was covalently coupled to the two cysteine residues Cys317 and Cys326 near the substrate-binding site of PKM2 (FIG. 7C).

Experimental Procedures

In-solution tryptic digestion of PKM2 for mass spectral analysis. PKM2 protein was reduced by 30 mM dithiothreitol at 37° C. for 1 hour, and then alkylated by treating with 30 mM iodoacetamide at room temperature in the dark for 1 hour. The alkylated protein was diluted 4-fold with 25 mM ammonium bicarbonate buffer (pH 8.5), and then incubated overnight at 37° C. with sequencing-grade modified trypsin (Promega, Madison, Wis., USA) at an enzyme to substrate ratio of 1:30 (w/w). The tryptic peptides were dried completely under vacuum. The peptide mixtures were desalted by C18 Zip-tip (Millipore) and subjected to mass spectrometric analysis.

NanoLC-MS/MS Analysis and MS/MS Database Searching. The tryptic peptides were analyzed on an LTQ-Orbitrap Fusion mass spectrometer (Thermo Fisher Scientific, San Jose, Calif.) coupled to an Agilent 1100 Series binary high-performance liquid chromatography pump (Agilent Technologies, Palo Alto, Calif., USA), and a FAMOS autosampler (LC Packing, San Francisco, Calif., USA). A total of 5 µL of samples were injected into a manually packed precolumn (150 µm ID×30 mm, 5 µm, 200 Å) at a 10 µL/min flow rate. Chromatographic separation was performed over 60 min on a manually packed reversed phase C18 nanocolumn (75 µm ID×200 mm, 3 µm, 200 Å) using 0.1% formic acid in water as mobile phase A, 0.1% formic acid in 80% acetonitrile as mobile phase B, and a split flow rate of 300 µL/min. The dynamics exclusion duration was set at 120 s, with a range in mass tolerance of ±25 ppm. The scan sequence began with an MS1 spectrum (Orbitrap analysis; resolution 120,000 at 200 m/z; mass range 200-2,000 m/z; automatic gain control (AGC) was set to accumulate 2×10$^5$ ions, with a maximum injection time of 200 ms). The most-abundant MS1 ions of charge states 2-7 were selected and fragmented using a top-speed approach (cycle time of 3 s). MS2 analysis was composed of higher-energy C-trap dissociation (HCD) (Orbitrap analysis; AGC 5×10$^4$; normalized collision energy (NCE) 28; maximum injection time 250 ms).

All MS and MS/MS raw data were processed with Proteome Discoverer version 2.1 (Thermo Scientific), and the peptides were identified from the MS/MS data searched against the target PKM2 human protein sequence (UniProtKB, P14618-1, isoform M2 of Pyruvate kinase PKM) database using the Mascot search engine 2.3.02 (Matrix Science). Search criteria used were as follows: trypsin digestion; considered variable modifications of serines, threonines, and tyrosines phosphorylation (+79.9663 Da), cysteine compound 1-modification (peptides molecular+ 516.1773 Da), glutamine deamidation (+0.98402 Da), methionine oxidation (+15.9949 Da), and cysteine carboxyamidomethylation (+57.0214 Da); up to three missed cleavages were allowed; and mass accuracy of 5 ppm for the parent ion and 0.05 Da for the fragment ions. The significant peptide hits defined as peptide score must be higher than Mascot significance threshold (*P<0.05) and therefore considered highly reliable, and that manual interpretation confirmed agreement between spectra and peptide sequence. The false discovery rate (FDR) of the peptides and protein groups was set to 1% for the MS/MS spectra automatically processed by Proteome Discoverer for statistical validation and quantification.

Figure 8:
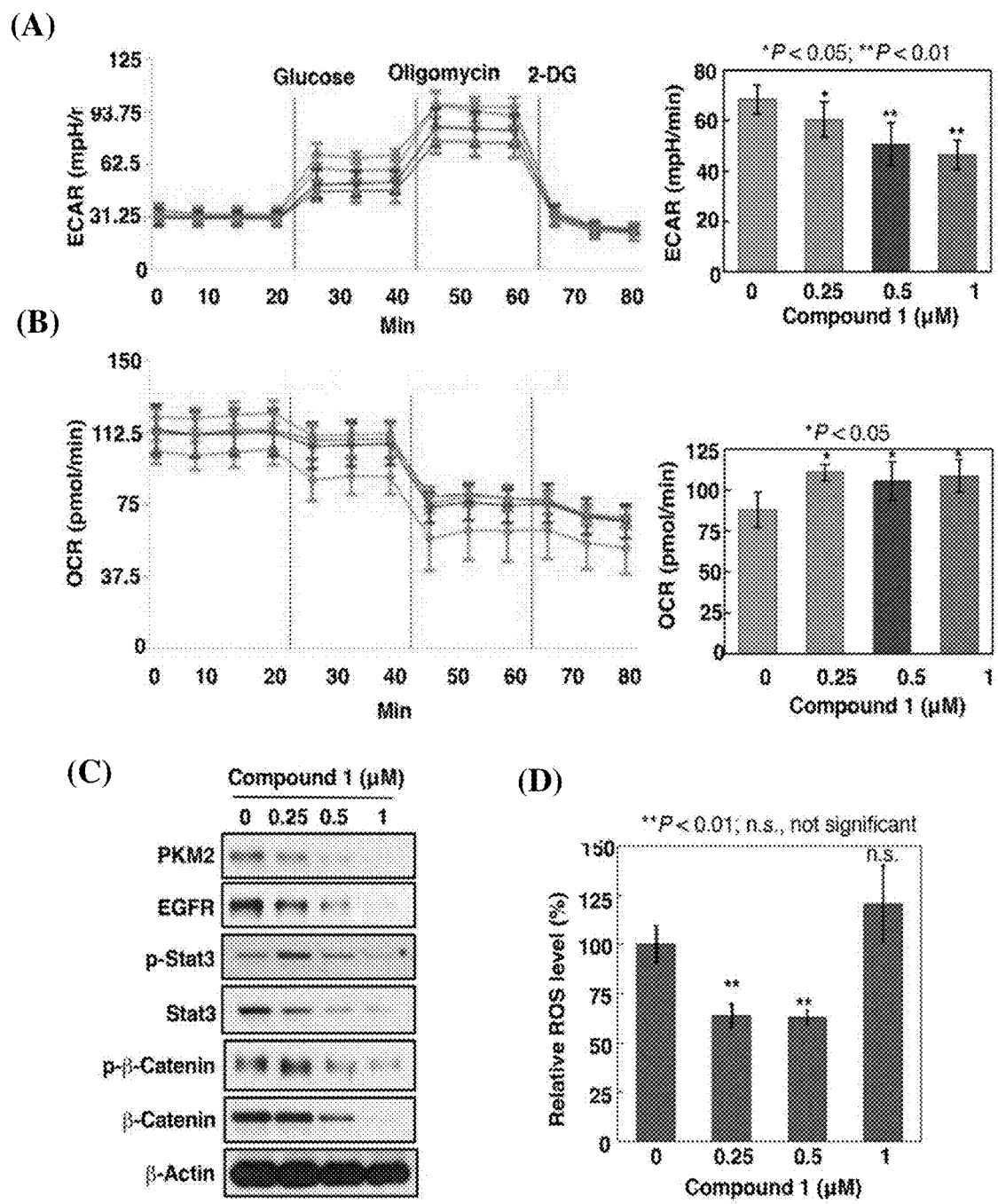
FIG. 8. Evidence that compound 1 target both metabolic and oncogenic functions in PC-9 cells. (A) Left, a representative graph of ECAR outputs in response to vehicle control (blue) or compound 1 at 0.25 µM (beige), 0.5 µM (green), and 1 µM (red). Glycolytic stress tests were performed using the Seahorse XF bioanalyzer to measure the glycolytic capacity of PC-9 cells. Right, average values of key parameters for the evaluation of glycolytic function with or without compound 1. Bar, means±S.D. (n=6). *P<0.05, **P<0.01. (B) Left, a representative graph of OCAR outputs in response to vehicle control (blue) or compound 1 at 0.25 µM (beige), 0.5 µM (green), and 1 µM (red). Right, average values of key parameters for the evaluation of mitochondrial functions with or without compound 1. Bar, means±S.D. (n=6). *P<0.05. (C) Western blot analyses of the concentration-dependent suppressive effect of compound 1 on the expression and/or phosphorylation of PKM2, EGFR, Stat3, β-Catenin in PC-9 cells. (D) Effect of compound 1 at indicated concentrations on ROS production in PC-9 cells. Bar, means±S.D. (n=3). P<0.01.

Example 6. Effects of Compound 1 on Glycolysis and Oncogenic Signaling in Cancer Cells In light of the role of PKM2 in promoting glycolysis, we hypothesized that the antitumor activity of compound 1 might, in part, be attributable to its ability to reverse the glycolytic phenotype (i.e., Warburg effect) of cancer cells. Accordingly, we examined the effects of compound 1 on the extracellular acidification rate (ECAR) and cellular oxygen consumption rate (OCR) in PC-9 cells, which represent key bioenergetic parameters of glycolysis (lactate production) and mitochondrial respiration (oxidative phosphorylation), respectively, using a commercial kit (Agilent Seahorse XF Glycolysis Stress Test Kit). In the ECAR measurement, glucose, oligomycin (an ATP synthetase inhibitor), and 2-deoxyglucose (2-DG; a hexokinase/glycolysis inhibitor) were added in tandem to glucose-starved cells at different time intervals to activate or interfere with glycolysis, thereby allowing the calculation of the glycolytic flux and glycolytic capacity. As shown, although compound 1 had no appreciable effect on the non-glycolytic acidification (i.e., the basal state prior to glucose injection), this PKM2 inhibitor suppressed the glycolytic acidification in a concentration-dependent manner (FIG. 8A). Meanwhile, the OCR response, a parameter for oxidative phosphorylation, was concurrently monitored. Relative to DMSO control, compound 1 was able to increase oxygen consumption in the basal state (prior to glucose supplementation), suggesting its ability to elevate mitochondrial respiration (FIG. 8B). It is noteworthy that when glucose was added to the basal medium, there was a decrease in the OCR in the control group. This phenomenon was previously referred to as the "Crabtree effect", i.e., when glucose is added to activate glycolysis, it might be more favorable for cells to generate ATP through substrate-level phosphorylation, thereby reducing the need of oxidative phosphorylation. However, this glucose-induced drop in OCR became less apparent in the presence of compound 1, which might be associated with the ability of compound 1 to block glycolysis.

Beyond its function as a metabolic regulator, PKM2 has also been reported to activate a number of oncogenic effectors through physical interactions in different cellular compartments, leading to increased protein stability [i.e., EGFR] or phosphorylation [i.e., Stat3 and β-catenin]. Thus, the effect of compound 1 on the expression and/or phosphorylation of these interacting partners was examined. As shown, treatment with compound 1 downregulated the expression of PKM2 and EGFR, accompanied by parallel decreases in the phosphorylation and expression of Stat3 and β-catenin in PC-9 cells (FIG. 8C). We rationalized that covalent modifications of PKM2 by compound 1 might decrease its protein stability, leading to decreases in the observed protein expression level. Although it has been reported that PKM2 regulated EGFR protein stability, the mechanism by which compound 1 decreased the expression levels of Stat3 and β-catenin remained unclear, which warrants investigation. It is interesting to note that the suppressive effect of compound 1 at 0.25 µM on Stat3 and β-catenin expression was accompanied by increased phosphorylation of these two oncoproteins. It is plausible that this increase in phosphorylation might be attributable to a compensatory mechanism in response to reduced protein expression in drug-treated cells. Moreover, as PKM2 has been reported to be negatively regulated by reactive oxygen species (ROS), we examined the effect of compound 1 on ROS production in PC-9 cells. As shown, compound 1 at 0.25 µM and 0.5 µM reduced the ROS level (FIG. 8D), which refuted the possibility that compound 1 might, in part, inhibit PKM2 through ROS. Together, these findings demonstrated the ability of compound 1 to target both metabolic and non-metabolic functions of cancer cells, at least in part, through irreversible inhibition of PKM2, which underlies its high antiproliferative potency.

Experimental Procedures

Glycolysis Stress assay. Extracellular acidification rate (ECAR) and oxygen consumption rate (OCR) were measured using a Seahorse Bioscience XF96 extracellular flux analyzer (Seahorse Bioscience) according to the manufacturer's protocol. PC-9 ells ($5 \times 10^4$) were seeded in 96 Seahorse XF Cell Culture Microplate with normal growth medium 24 hours before treatment with compounds. The cells were treated with DMSO or compound 1 for 4 hours at 37° C. under 5% $CO_2$ atmosphere. After 4 hours, the culture medium was replaced with glycolysis optimization medium and incubated at 37° C. without $CO_2$ for 1 hour prior to assay. The ECAR and OCAR measurement trace during Seahorse Glycolysis Stress Assay in which the control and compound 1 treated PC-9 cells was injected with of 10 mM Glucose, 1 µM Oligomycin and 50 mM 2-DG. Every point represents the average of six different wells.

Immunoblot analysis. PC-9 cells were seeded into 6 cm dish at a concentration of $5 \times 10^5$ cells/mL. After 24 hours, cells were treated with 0-1 µM compound 1 or DMSO alone for 24 hours. The cells were harvested at 24 hours, and protein extractions were carried out. The protein lysate was subjected to 10% SDS-PAGE and transferred to a nitrocellulose membrane (GE Healthcare Life Sciences). Protein expression was analyzed by Western blotting using primary antibodies against PKM2, EGFR, p-STAT3, STAT3, p-β-catenin (Cell Signaling Technology), β-catenin (Santa Cruz Biotechnology) and β-actin (Sigma-Aldrich), followed by incubation with horseradish peroxidase-conjugated secondary (Jackson ImmunoResearch Laboratories). Specific proteins were detected by chemiluminescence using ECL Plus Western Blotting Detection Reagents (GE Healthcare Biosciences).

ROS assay. ROS detection was performed by using a fluorescent assay kit from BioVision (Milpitas, Calif., USA) according to the manufacturer's instructions. Briefly, PC-9 cells were seeded into 96-well plate at a cell density of $2 \times 10^4$ cells per well. After 24 hours, cells were treated with indicated concentration of compound 1 or DMSO for 6 hours. After treatment, cells were washed in ROS assay buffer and then incubated with 1×ROS label diluted in ROS assay buffer for 45 min at 37° C. in the dark. The ROS label was removed, and the fluorescence at Ex/Em 495/529 nm in end point mode was measured immediately after 100 µl of ROS assay buffer was added to each well.

Example 7. In Vivo Efficacy of Compound 1 in Suppressing the Growth of PC-9 Xenograft Tumors in Nude Mice Pursuant to the above in vitro findings, we evaluated the in vivo tumor-suppressive efficacy of compound 1 in an ectopic PC-9 xenograft tumor model. Athymic nude mice bearing established subcutaneous PC-9 tumors were randomly divided into two groups (n=8 for each group; initial tumor volume: vehicle, 50±11 $mm^3$; compound 1, 53±6 $mm^3$), and were treated once daily with compound 1 at 10 mg/kg or vehicle via intraperitoneal injection. As shown, compound 1 significantly suppressed tumor growth, as indicated by tumor volume and tumor weight, relative to the vehicle control after 25 days of treatment (***$P<0.001$) (FIG. 9A). No appreciable weight loss was noted in the drug-treated group relative to control (FIG. 9B), suggesting that compound 1 did not show overt toxicity over the course of 25-day treatment. Moreover, Western blot analysis of tumor lysates showed that compound 1 treatment led to significant suppression of the expression of PKM2 and its binding partners EGFR, Stat3, and β-catenin, as compared to the vehicle control (FIG. 9C), indicating that tumor-suppressive activity correlated with the ability of compound 1 to target the expression of PKM2 and relevant non-metabolic biomarkers.

Experimental Procedures

In vivo efficacy study. Athymic nude mice were purchased from the National Laboratory Animal Center (Taipei, Taiwan). To assess the effect of compound 1 on tumor growth in vivo, $1 \times 10^6$ PC-9 cells were mixed with Matrigel (BD Biosciences) at a 1:1 ratio and subcutaneously implanted into nude mice (6-week-old, female; a total of 16 mice). After 7 days, mice were treated with once daily vehicle or 10 mg/kg compound 1 in sterile water containing 0.5% methylcellulose (w/v)+0.1% Tween-80 (v/v) (n=8 for each group). Tumors were measured with calipers and volumes were calculated using V=(width$^2$×length)×0.52. On day 25, tumors were excised and weighed. Tumor specimens were collected, and expression of target proteins in tumor lysates were analyzed by Western blotting, which were quantified by ImageJ. according to a published online procedure. (https://openwetware.org/wiki/Protein_Quantification_Using_ImageJ).

Statistical analysis. In vitro experiments were performed in triplicate, of which and data were presented as means±S.D. Group means were analyzed by using one-way ANOVA, followed by t test. For the in vivo experiments, differences in tumor volume and tumor weight were analyzed by log-rank test and Student's t-test, respectively. Differences were considered significant at *$P<0.05$, $P<0.01$, *$P<0.001$.

Figure 10:
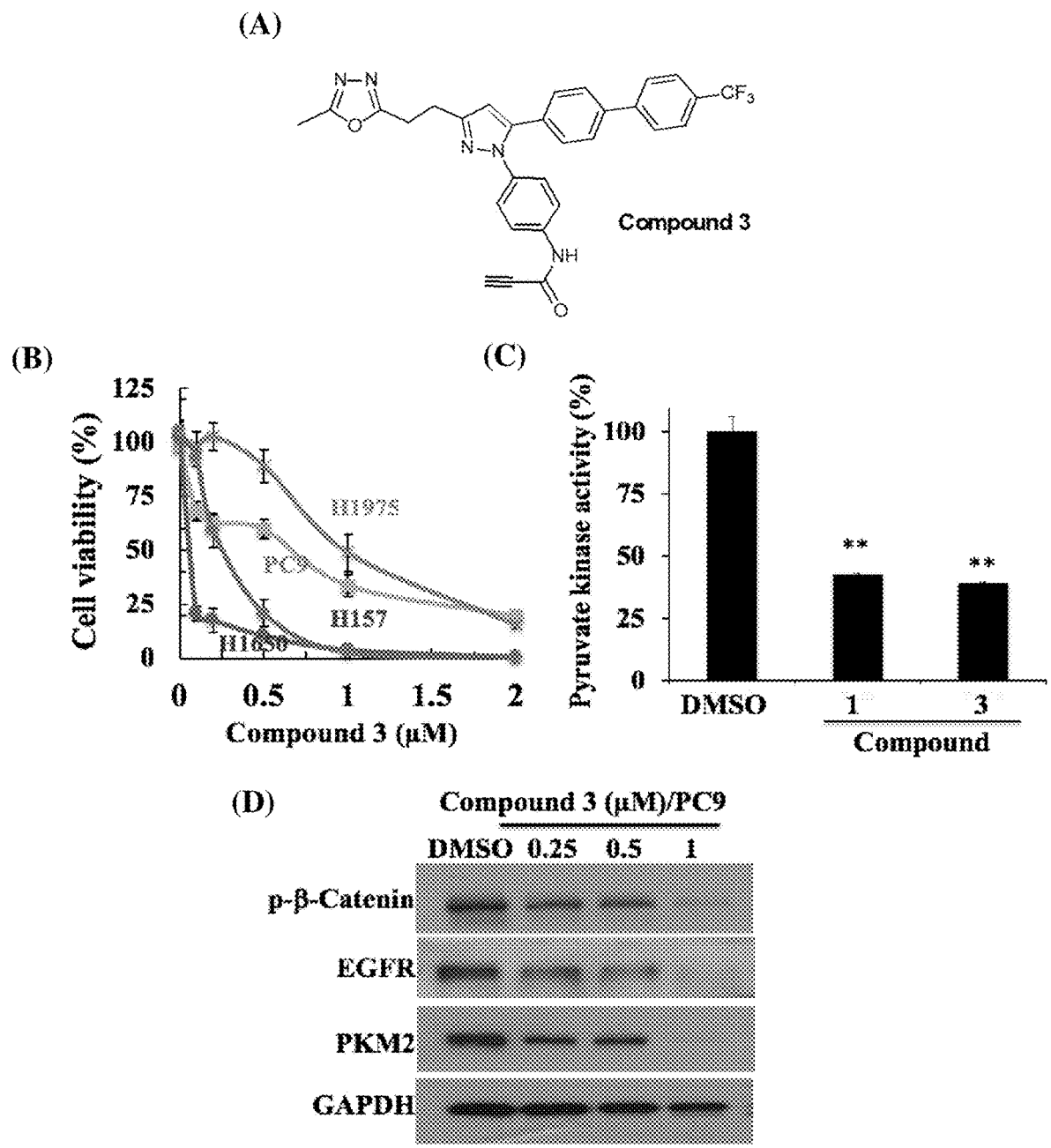
FIG. 10. (A) Structure of compound 3. (B) Compound 3 exhibited high antiproliferative potencies against a panel of lung cancer cell lines. (C) Compound 3 was equipotent in inhibiting PKM2 kinase activity in PC-9 cells. (D) Concentration-dependent effect of compound 3 on the phosphorylation/expression of various oncogenic biomarkers, including β-catenin, EGFR, and PKM2.

Example 8. The carboxamide moiety [—C(=O)NHCH$_3$] of compound 1 was amenable to structural modifications via a bioisosteric replacement strategy to generate new derivatives without compromising the PKM2 kinase-inhibiting activity. Bioisosteric replacement represents a common strategy for lead optimization in the course of drug development. We here disclosed the development of compound 3 via this strategy, in which the carboxamide moiety [—C(=O)NHCH$_3$] of compound 1 was replaced by a 5-methyl-substituted 1,3,4-oxadiazole ring (structure, FIG. 10A). Compound 3 exhibited high antiproliferative potencies against different lung cancer cell lines (FIG. 10B), and was equipotent in suppressing PKM2 kinase activity relative to compound 1. In addition, Western blot analysis shows its high efficacy in suppressing the phosphorylation/expression of various oncogenic biomarkers, including β-catenin, EGFR, and PKM2 (FIG. 10D).

What is claimed is:

1. A compound of the general formula I:

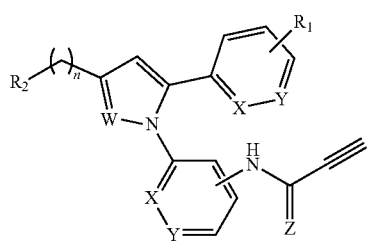

Formula 1 wherein

R$_1$ is independently selected from aryl, heteroaryl or heterocyclyl in any position, optionally substituted with halogen, C$_1$-C$_6$ alkyl, C$_2$-C$_6$ alkenyl, C$_2$-C$_6$ alkynyl, CN, haloalkyl, alkylamino, or C$_{1-6}$ alkoxy;

R$_2$ is independently selected from —C(=O) NR$_3$R$_4$ or —C(=S) NR$_3$R$_4$ wherein R$_3$ and R$_4$ are the same or different and each is H, C$_1$-C$_6$ alkyl, branched alkyl, C$_2$-C$_6$ alkenyl, branched alkenyl, or C$_3$-C$_6$ cycloalkyl which is optionally substituted with OH, CN, methoxy, C$_1$-C$_6$ alkyloxyalkyl, C$_1$-C$_6$ alkylamino, C$_1$-C$_6$ alkylaminoalkyl, aryl, heteroaryl, cycloalkyl, or heterocycloalkyl;

W is independently selected from carbon or nitrogen;

X and Y are independently selected from carbon or nitrogen;

Z is independently selected from oxygen or sulfur; and n is independently selected from 1 to 6.

2. The compound according to claim 1, wherein W is nitrogen.

3. The compound according to claim 1, wherein W is carbon.

4. The compound according to claim 1 or 2, wherein Z is oxygen.

5. The compound according to claim 4, wherein R$_1$ is phenyl in any position, optionally substituted with halogen, C$_1$-C$_6$ alkyl, C$_2$-C$_6$ alkenyl, C$_2$-C$_6$ alkynyl, CN, haloalkyl, alkylamino, or C$_1$-C$_6$ alkoxy.

6. The compound according to claim 5, wherein R$_1$ is trifluoromethyl-phenyl.

7. The compound according to claim 5, wherein R$_1$ is (prop-2-yn-1-yloxy) benzene.

8. The compound according to claim 5, wherein R$_2$ is (methylamino)-carbonyl.

9. The compound according to claim 5, wherein R$_2$ is 5-methyl-1,3,4-oxadiazol-2-yl.

10. The compound of claim 1, wherein the compound is selected from the group of compounds:

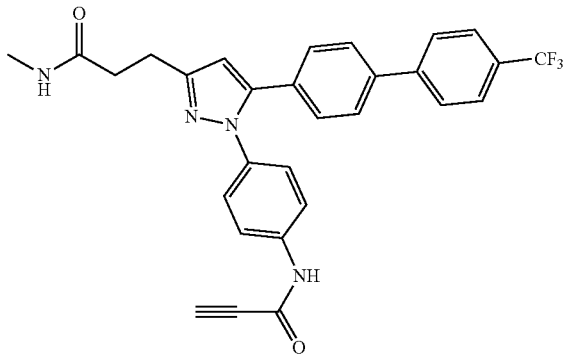

Compound 1

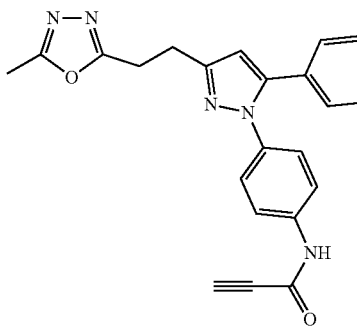

Compound 3

-continued

Compound 4

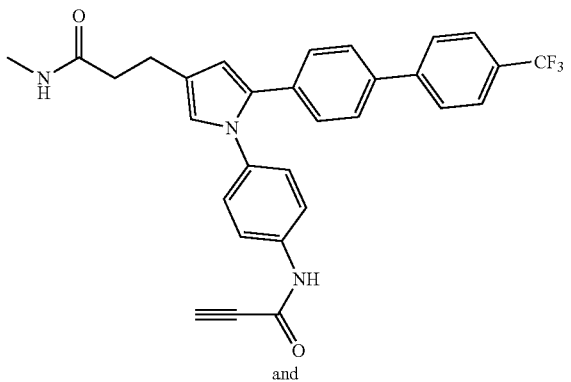

and

Compound 5

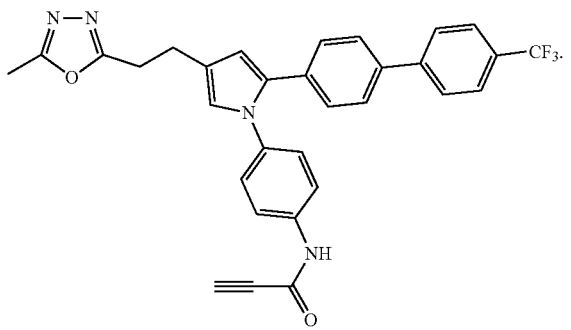

11. A pharmaceutical composition comprising a compound as claimed in claim 1, as well as a pharmaceutically acceptable carrier or diluent.

12. A method of inducing an anti-tumor effect in a subject suffering from tumor comprising administering to the subject a pharmaceutical composition comprising an effective amount of compound of formula I as claimed in claim 1 or a pharmaceutically acceptable forms thereof to the subject, wherein the tumor comprises pancreatic cancer, breast cancer, oral cancer, colon cancer, prostate cancer, or lung cancer.

13. The method of claim 12, wherein the anti-tumor effect is through inhibiting PKM2-mediated metabolic and non-metabolic functions of cancer cells.

14. The method of claim 12, wherein the anti-tumor effect is selected from the group consisting of reducing tumor volume, inhibiting tumor growth, inhibiting tumor progression, altering metabolic activity in a tumor, inducing quiescence in a tumor, inhibiting or reducing tumor invasiveness, and reducing tumor weight.

15. The method according to claim 12, wherein the tumor is aggressive cancer.

16. The method according to claim 15, wherein the aggressive cancer adopts glycolytic phenotype.

17. The method of claim 12, wherein the compound is a compound of claim 10.

* * * * *

SEQUENCE LISTING

```
<160> NUMBER OF SEQ ID NOS: 2

<210> SEQ ID NO 1
<211> LENGTH: 23
<212> TYPE: PRT
<213> ORGANISM: Homo sapiens

<400> SEQUENCE: 1

Ala Gly Lys Pro Val Ile Cys Ala Thr Gln Met Leu Glu Ser Met Ile
1               5                   10                  15

Lys Lys Pro Arg Pro Thr Arg
            20

<210> SEQ ID NO 2
<211> LENGTH: 8
<212> TYPE: PRT
<213> ORGANISM: Homo sapiens

<400> SEQUENCE: 2

Met Met Ile Gly Arg Cys Asn Arg
1               5
```